(12) United States Patent
Deutschle et al.

(10) Patent No.: US 9,862,519 B2
(45) Date of Patent: Jan. 9, 2018

(54) SUPPORTING STRUCTURE FOR CONCURRENTLY SUPPORTING A PLURALITY OF CONTAINERS FOR SUBSTANCES FOR MEDICAL, PHARMACEUTICAL OR COSMETIC APPLICATIONS

(71) Applicant: SCHOTT AG, Mainz (DE)

(72) Inventors: Gregor Fritz Deutschle, Wiesbaden (DE); Edgar Pawlowski, Stadecken-Elsheim (DE); Joern Wassenberg, Mainz (DE); Andreas Reisse, Regensburg (DE)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 14/533,134

(22) Filed: Nov. 5, 2014

(65) Prior Publication Data

US 2015/0122693 A1 May 7, 2015

(30) Foreign Application Priority Data

Nov. 5, 2013 (DE) .......................... 10 2013 112 167

(51) Int. Cl.
*B65B 7/28* (2006.01)
*B65D 1/36* (2006.01)
(Continued)

(52) U.S. Cl.
CPC ...... *B65D 1/36* (2013.01); *A61J 1/16* (2013.01); *B65B 3/003* (2013.01); *B65B 7/2821* (2013.01);
(Continued)

(58) Field of Classification Search
CPC ............. B65D 1/36; B65D 25/108; A61J 1/16
See application file for complete search history.

(56) References Cited

U.S. PATENT DOCUMENTS

| | | | | |
|---|---|---|---|---|
| 4,503,972 A | * | 3/1985 | Nelligan | B25H 3/003 206/369 |
| 4,736,838 A | * | 4/1988 | Nakata | A45C 11/34 206/214 |
| 4,770,297 A | * | 9/1988 | Chang | B65D 85/28 206/379 |
| 5,372,252 A | * | 12/1994 | Alexander | A61B 19/0288 206/210 |

(Continued)

FOREIGN PATENT DOCUMENTS

| | | |
|---|---|---|
| CN | 102470072 | 5/2012 |
| WO | 2009015862 A1 | 2/2009 |
| WO | 2011135085 A1 | 11/2011 |

*Primary Examiner* — Anthony Stashick
*Assistant Examiner* — James Way
(74) *Attorney, Agent, or Firm* — Ohlandt, Greeley, Ruggiero & Perle, L.L.P.

(57) ABSTRACT

A supporting structure for concurrently supporting a plurality of containers having a predetermined length for medical, pharmaceutical or cosmetic applications comprises a carrier having a plurality of supporting means for supporting the containers on the carrier, optionally, at least in a first orientation (e.g. upright) or in a second orientation (upside-down or also upright).

Figure 1:
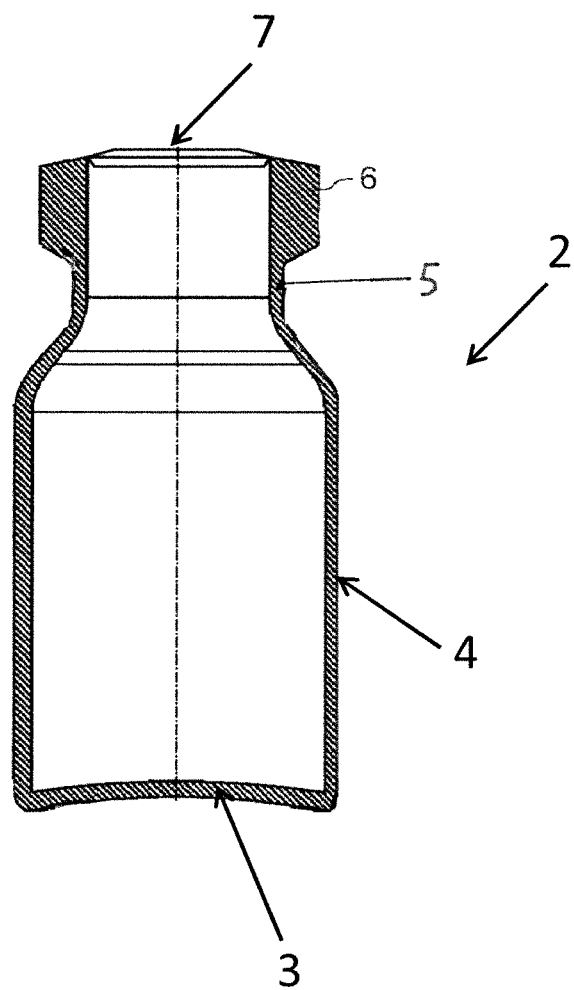

According to the invention the carrier is matched to the lengths of the containers such that the upper ends of the containers are arranged in the first position at the same distance to the carrier as the lower ends of the containers in the second position and that the upper ends and/or lower ends of the containers are accessible for a further processing of the containers while they are supported on the carrier.

Thus, there is no need to adjust the heights of processing stations in which the containers are treated or processed further, regardless of whether the containers are supported on the carrier in the first position or in the second position, because the upper ends and lower ends of the containers are disposed on the same height level in both positions (orientations) of the containers. According to the invention this facilitates the treatment and processing of containers con- (Continued)

siderably because the effort in terms of adjustment, control and automation can be considerably simplified.

26 Claims, 39 Drawing Sheets

(51) Int. Cl.
*B65D 25/10* (2006.01)
*B65D 77/04* (2006.01)
*B65D 85/42* (2006.01)
*B65B 3/00* (2006.01)
*A61J 1/16* (2006.01)
*A61M 5/00* (2006.01)
*B01L 9/06* (2006.01)

(52) U.S. Cl.
CPC ....... *B65D 25/108* (2013.01); *B65D 77/0446* (2013.01); *B65D 85/42* (2013.01); *A61M 5/002* (2013.01); *B01L 9/06* (2013.01); *B01L 2200/185* (2013.01); *B01L 2300/041* (2013.01); *B01L 2300/0829* (2013.01)

(56) References Cited

U.S. PATENT DOCUMENTS

| | | | |
|---|---|---|---|
| 5,525,314 A * | 6/1996 | Hurson | A61C 3/04 206/369 |
| 6,474,481 B1 * | 11/2002 | Liu | B25H 3/003 206/377 |
| 7,232,038 B2 * | 6/2007 | Whitney | B01L 9/06 211/74 |
| 7,910,067 B2 * | 3/2011 | Knight | B01L 9/06 211/71.01 |
| 8,100,263 B2 | 1/2012 | Vanderbush et al. | |
| 8,118,167 B2 * | 2/2012 | Togashi | A61B 19/026 206/519 |
| 2006/0016156 A1 * | 1/2006 | Bush | A61M 5/002 53/434 |
| 2009/0100802 A1 * | 4/2009 | Bush | A61M 5/002 53/434 |
| 2011/0226662 A1 * | 9/2011 | Nicoletti | B65D 5/503 206/562 |
| 2012/0103861 A1 * | 5/2012 | Song | A61M 5/008 206/563 |
| 2012/0181285 A1 | 7/2012 | Krauss | |

* cited by examiner

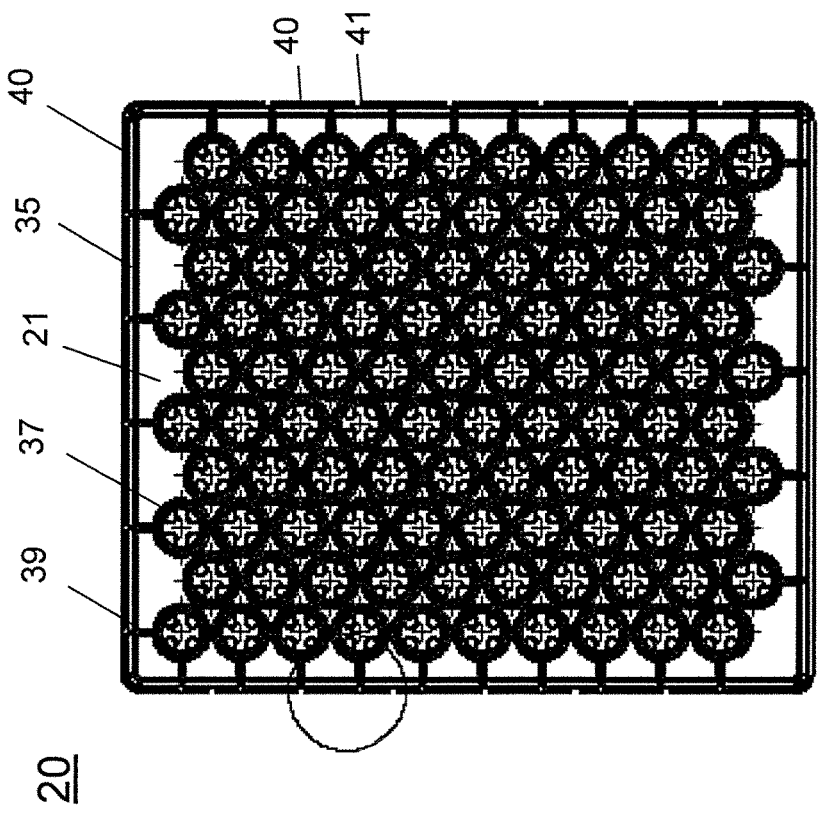
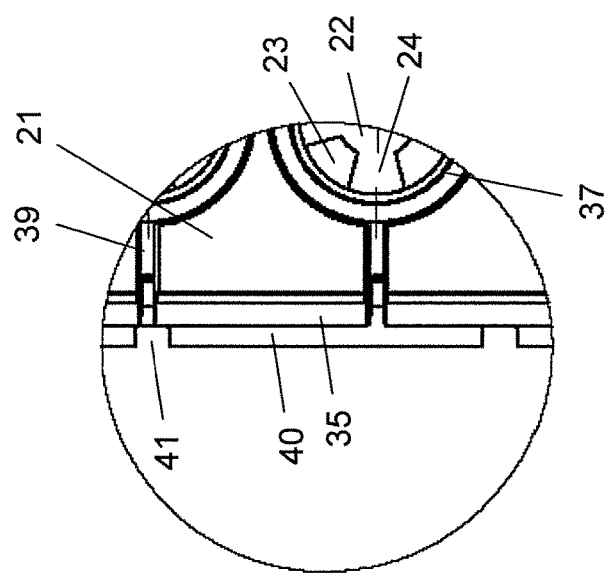
Fig. 2b
Fig. 2c

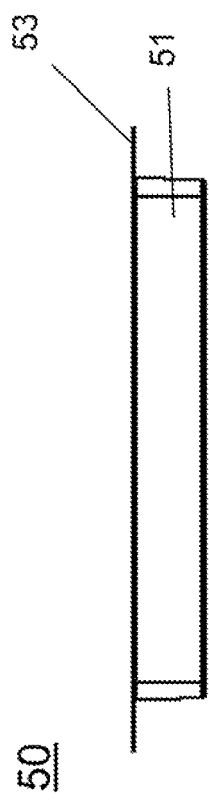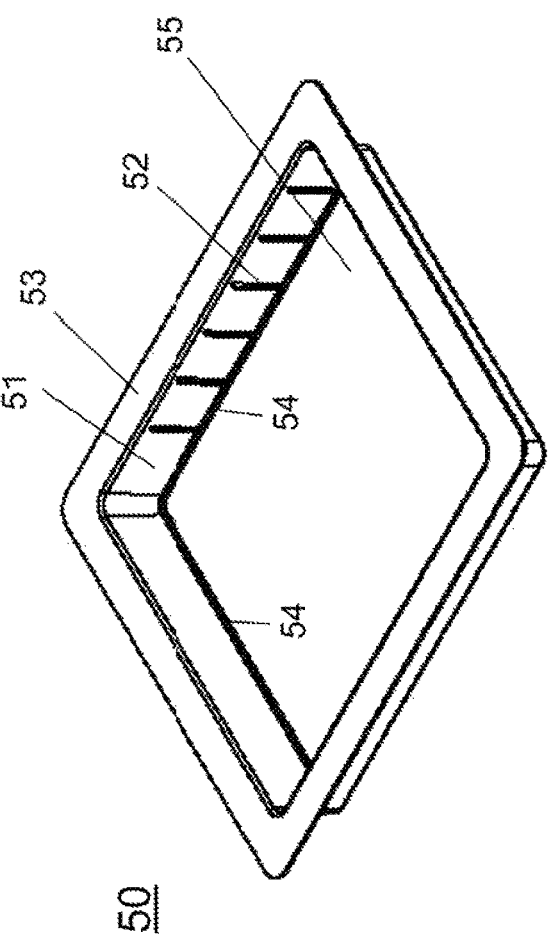

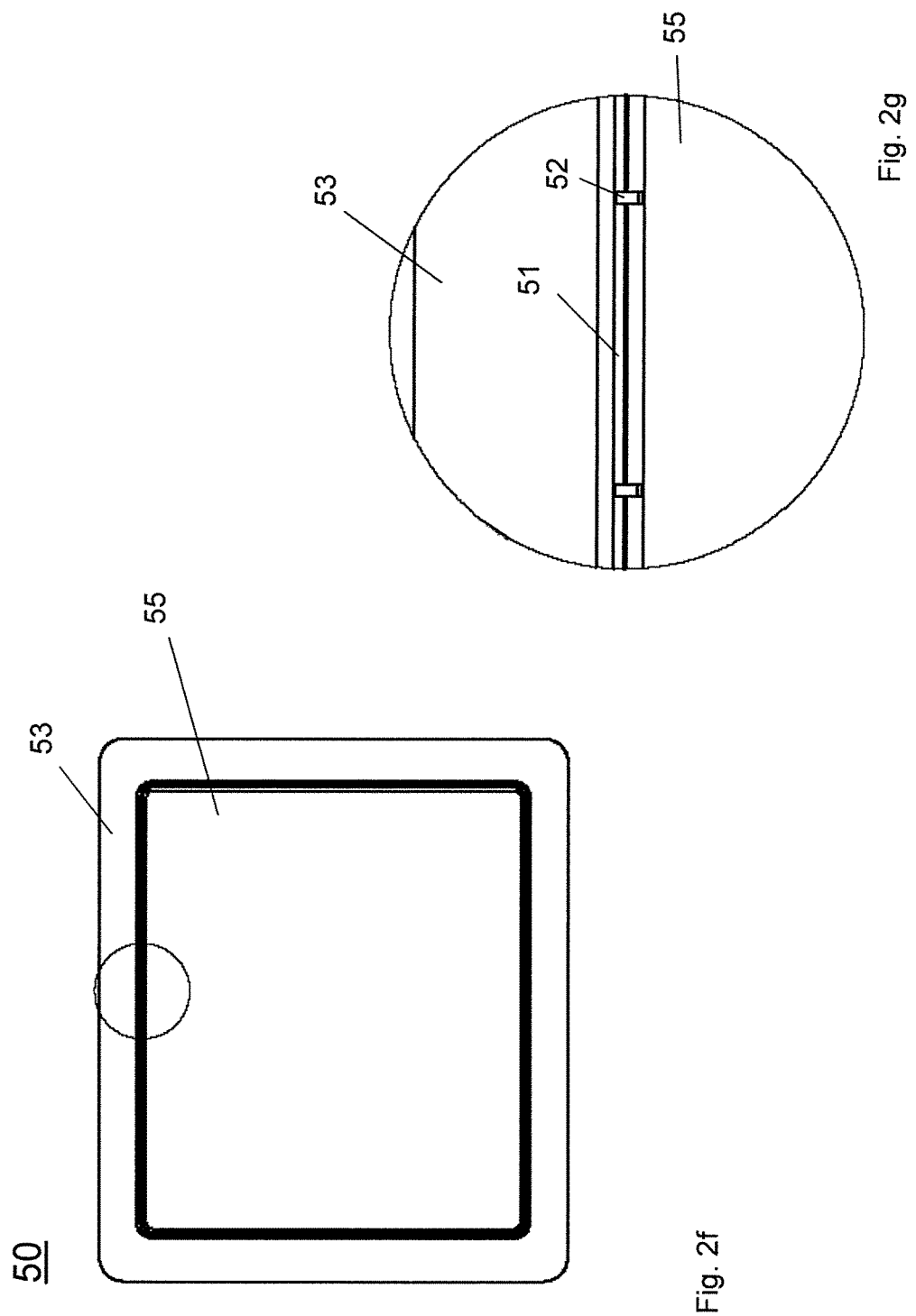

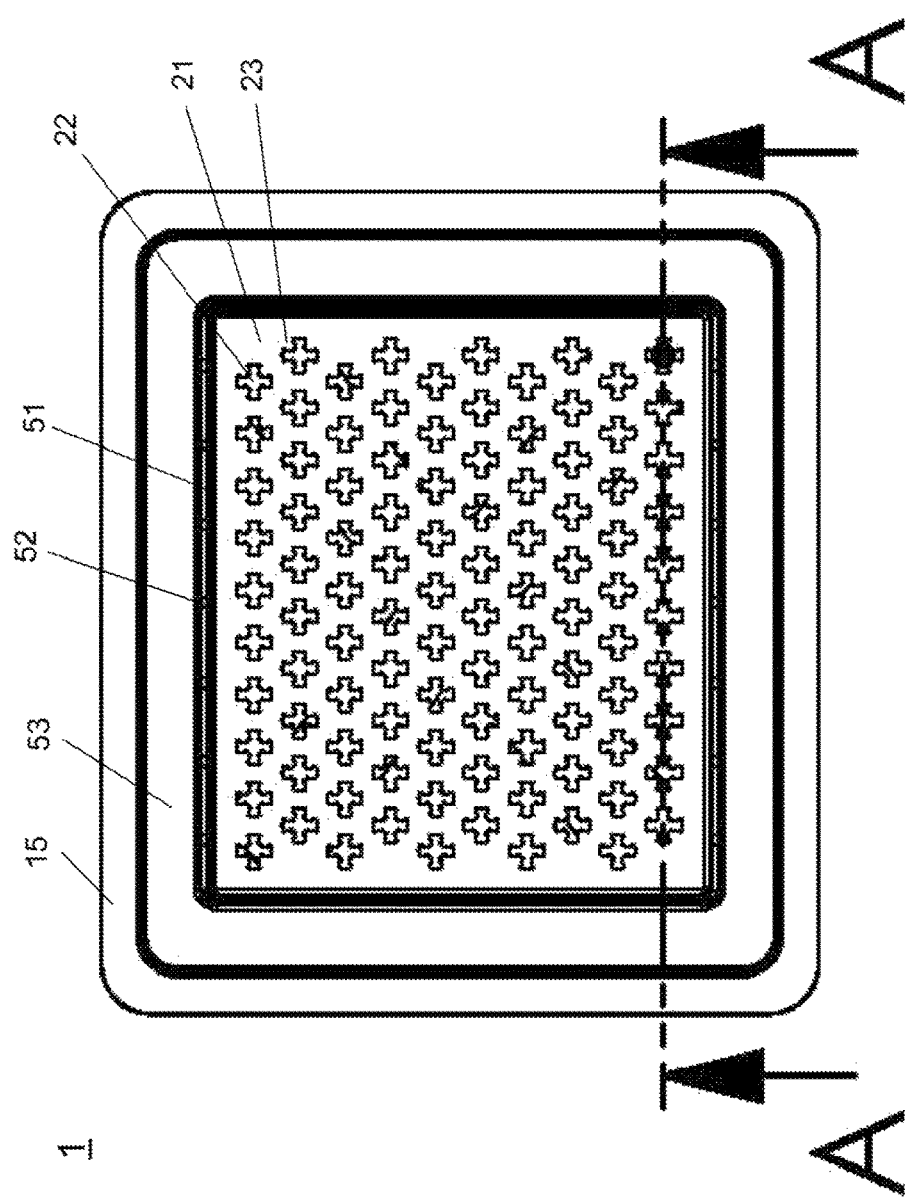

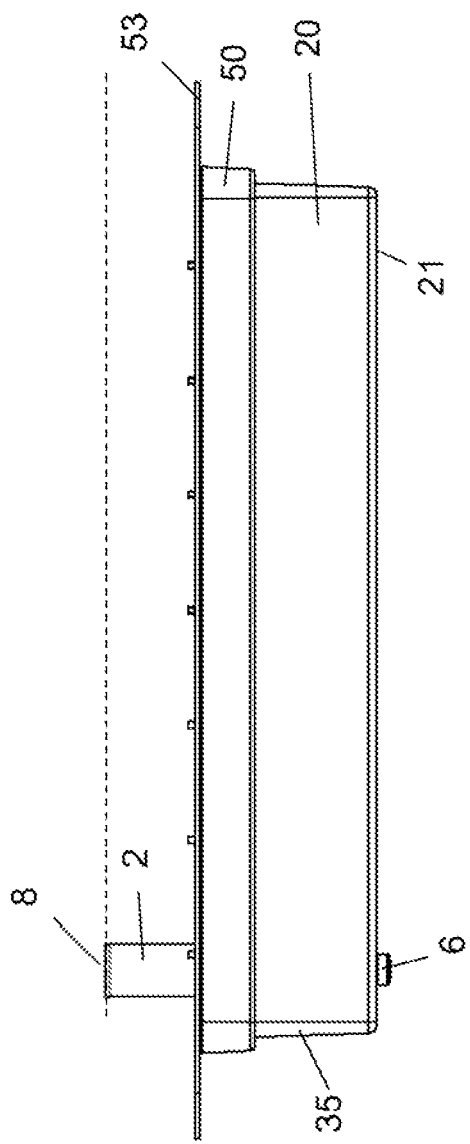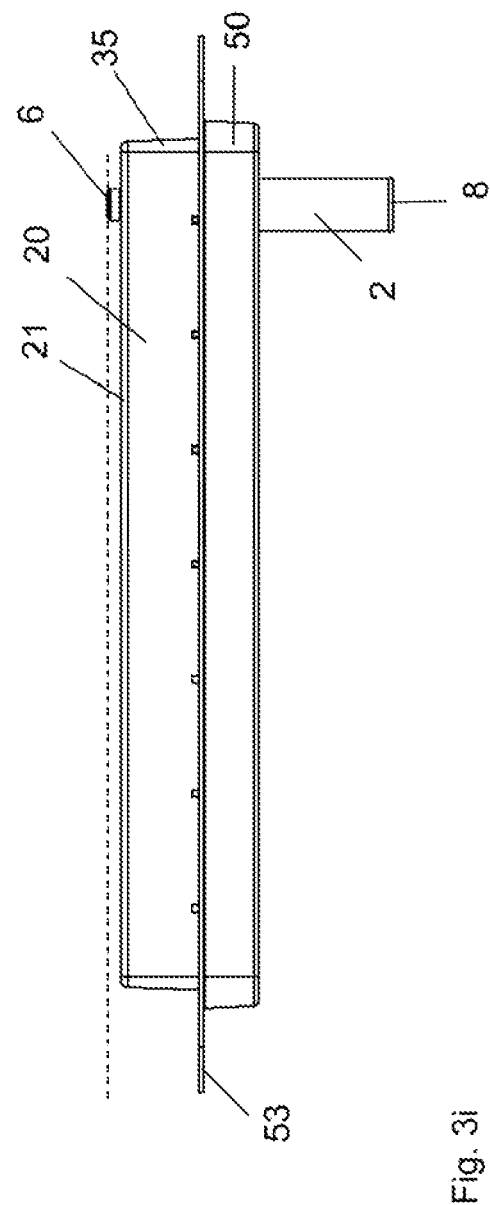

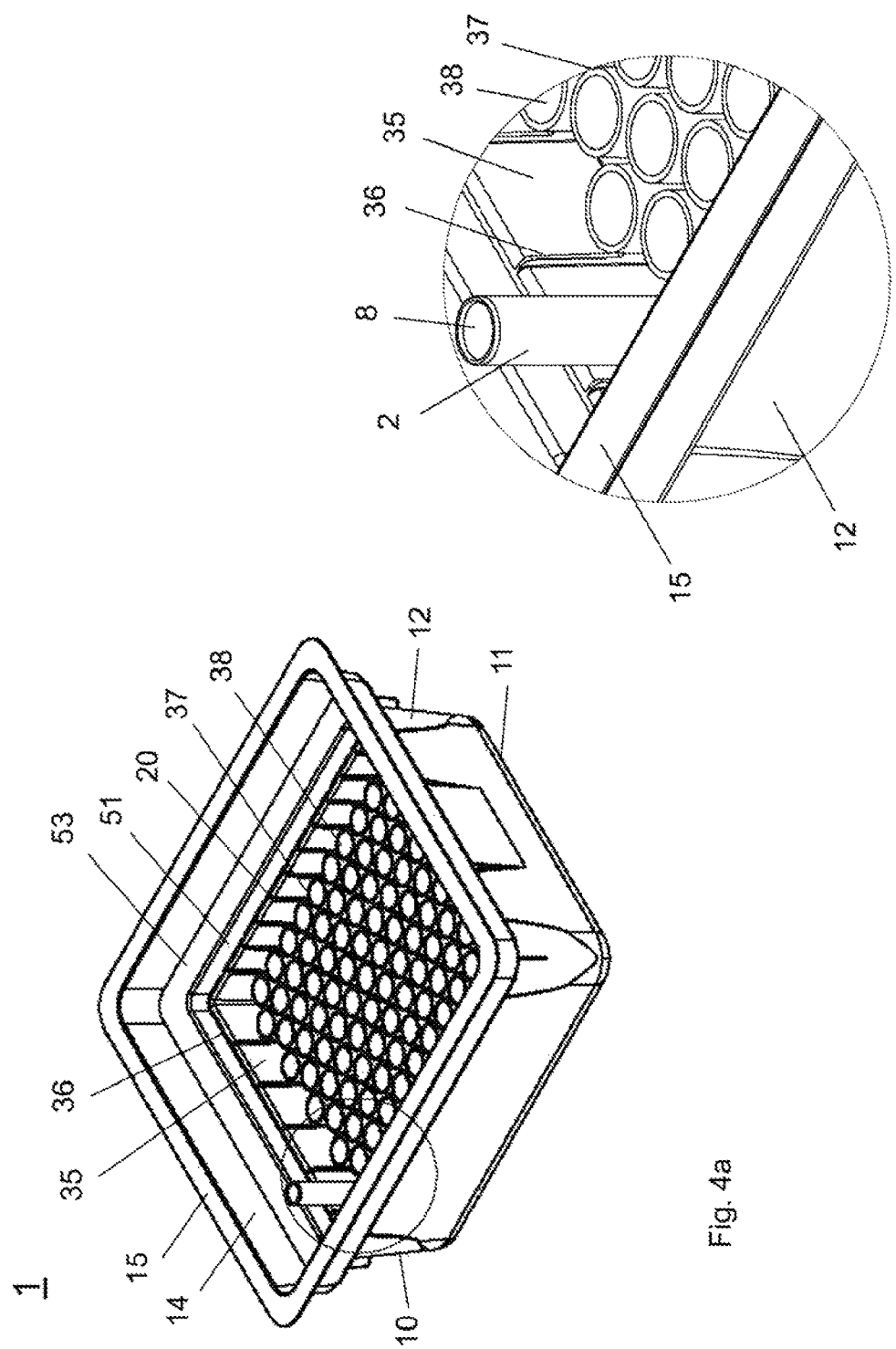

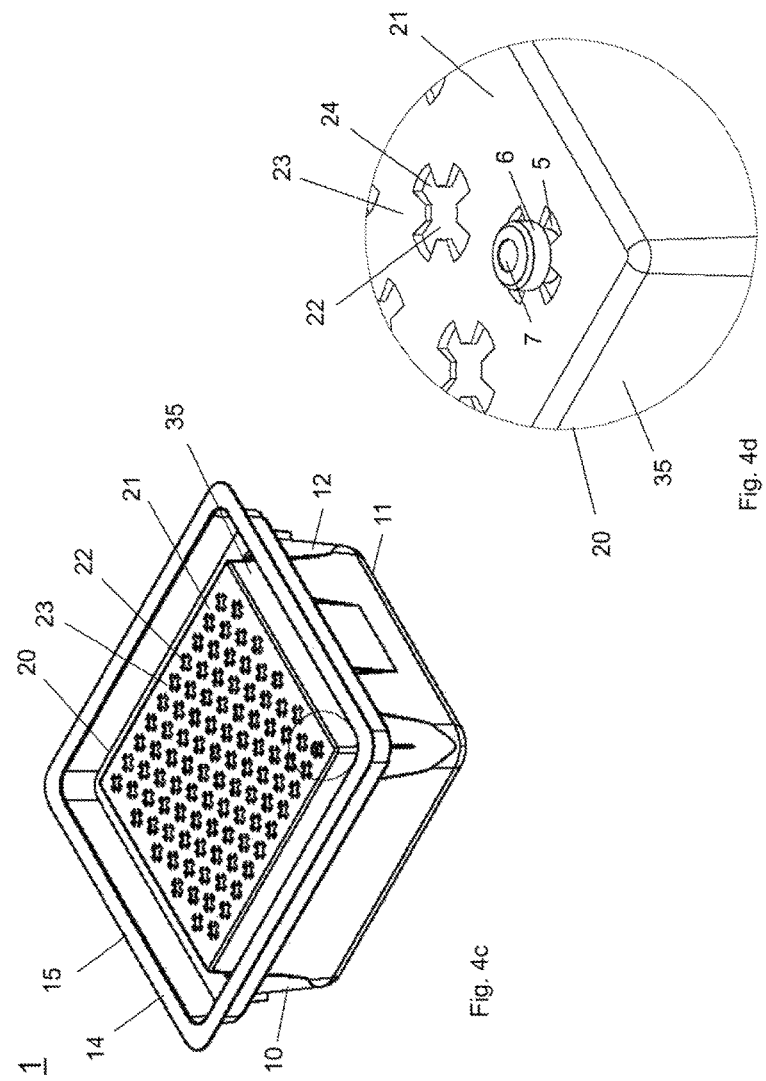

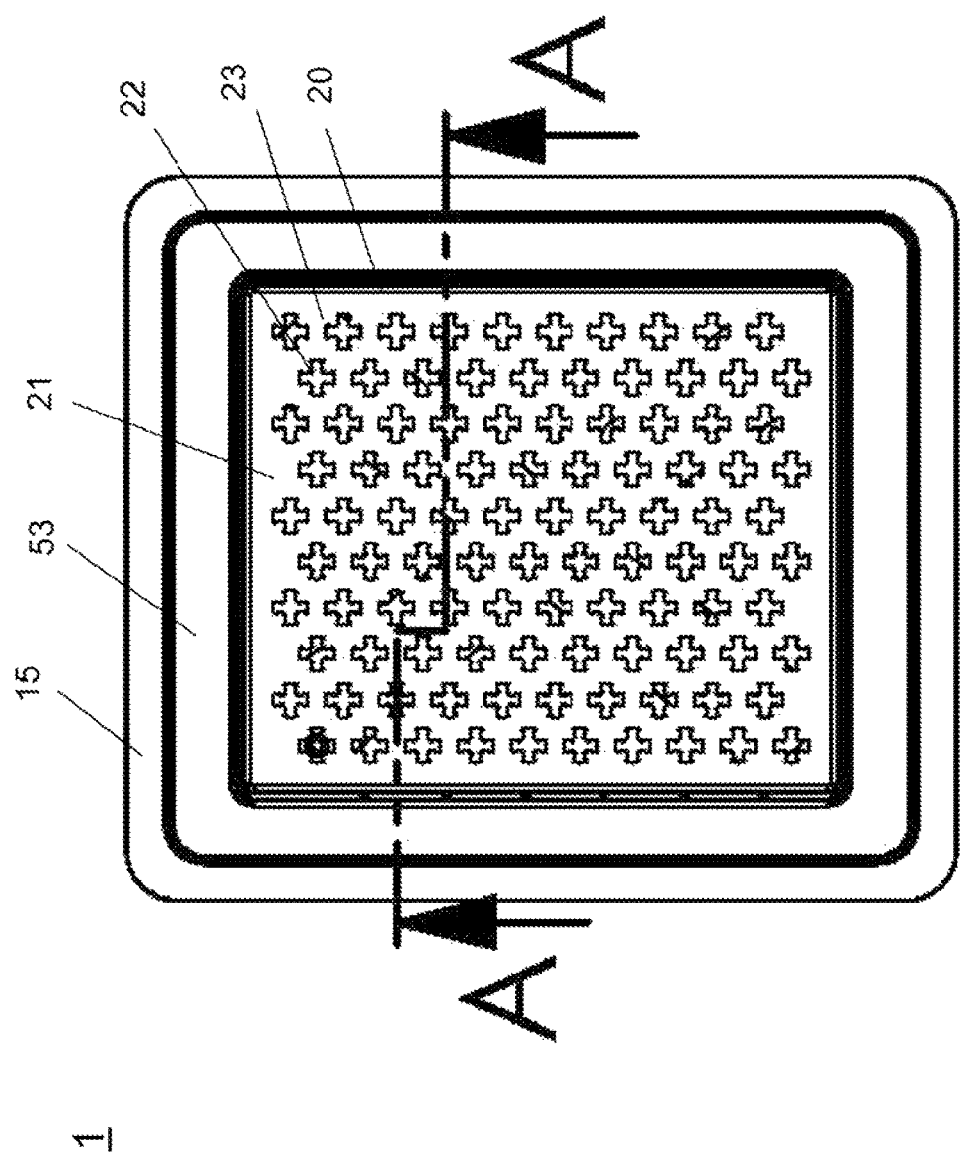

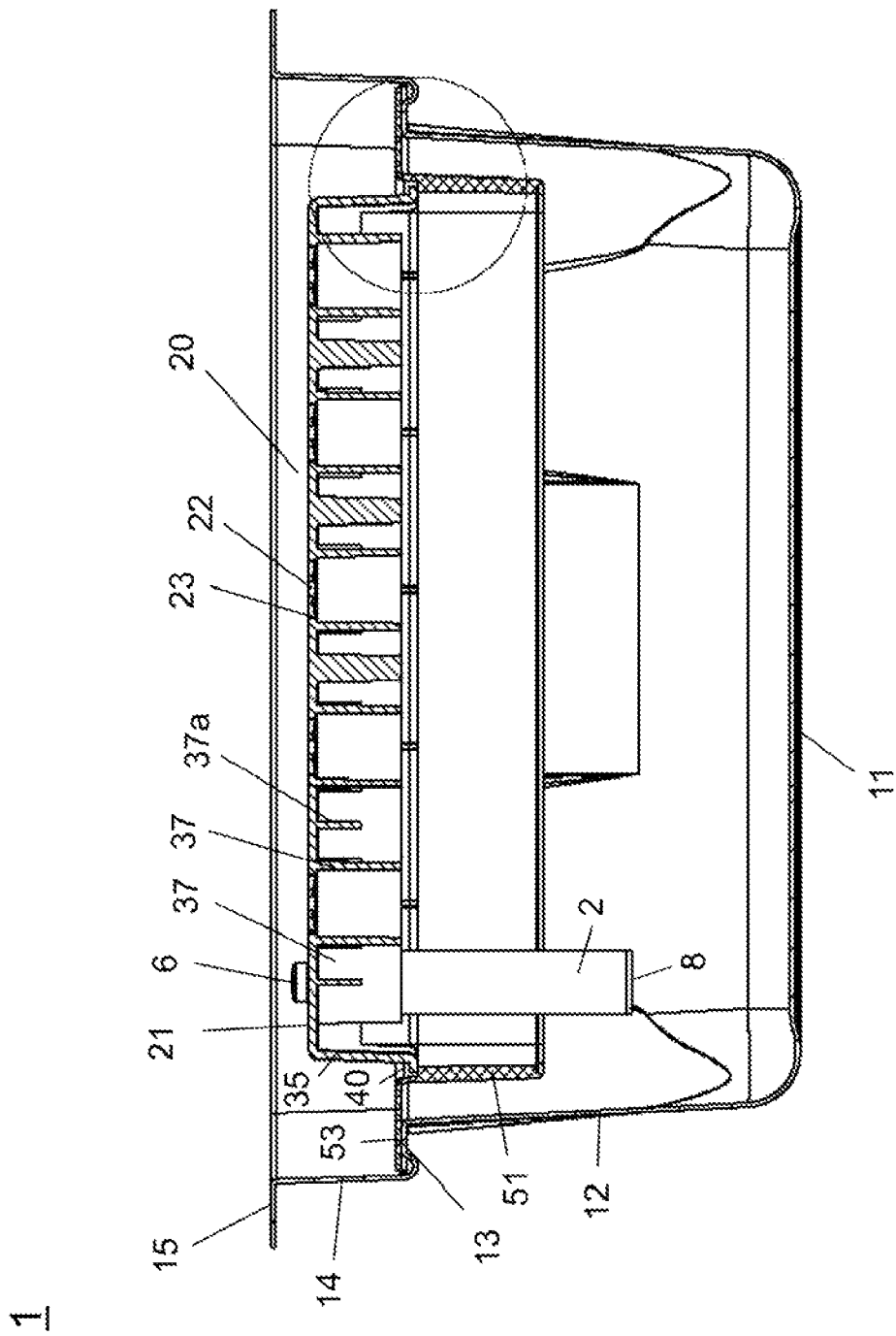

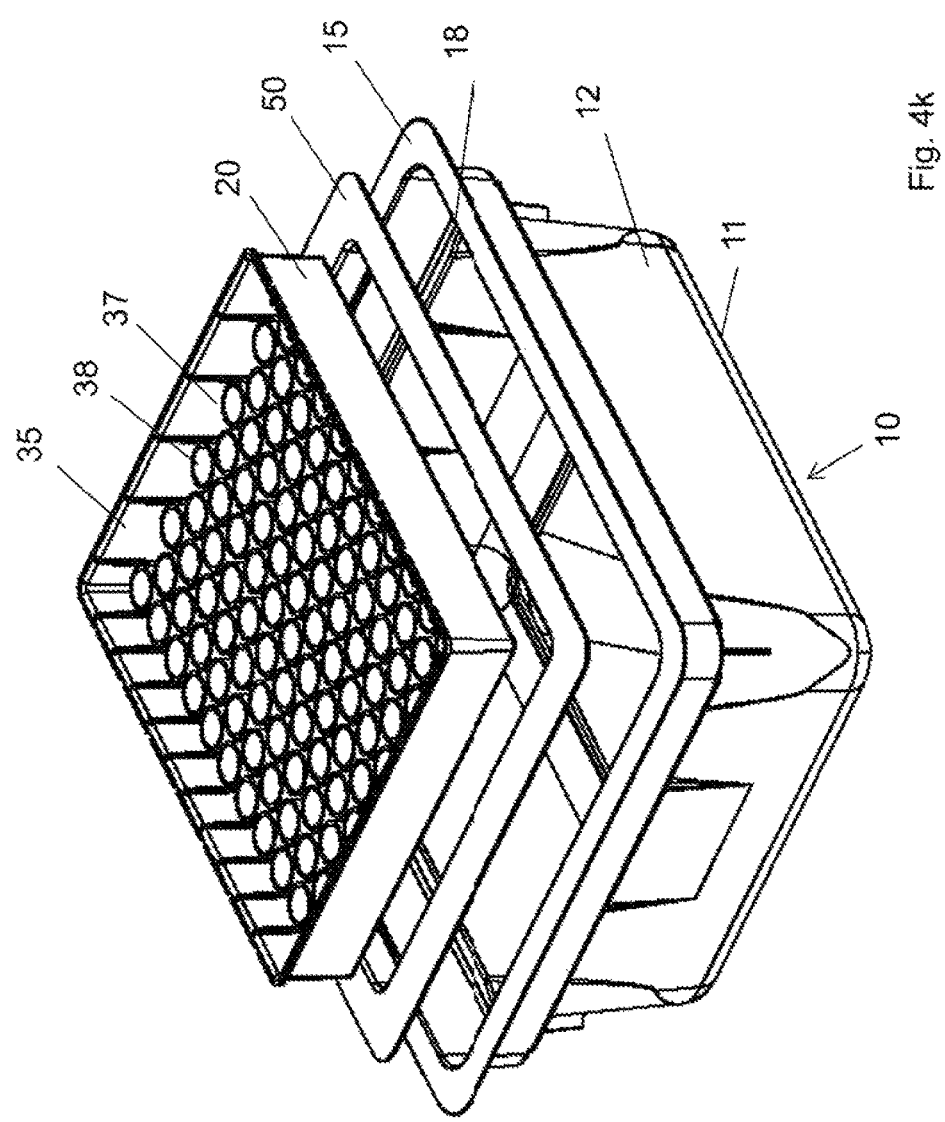

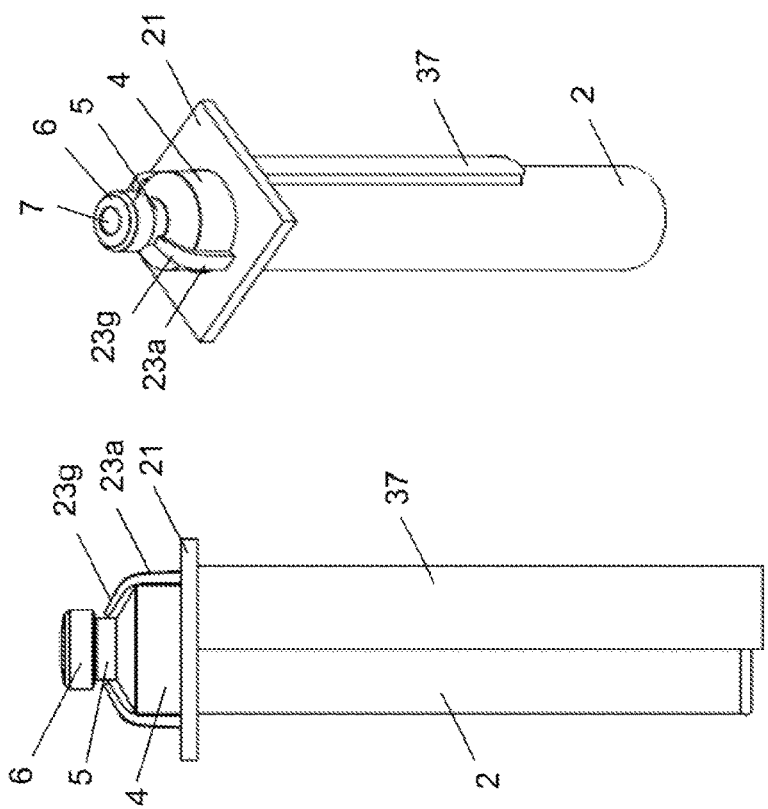
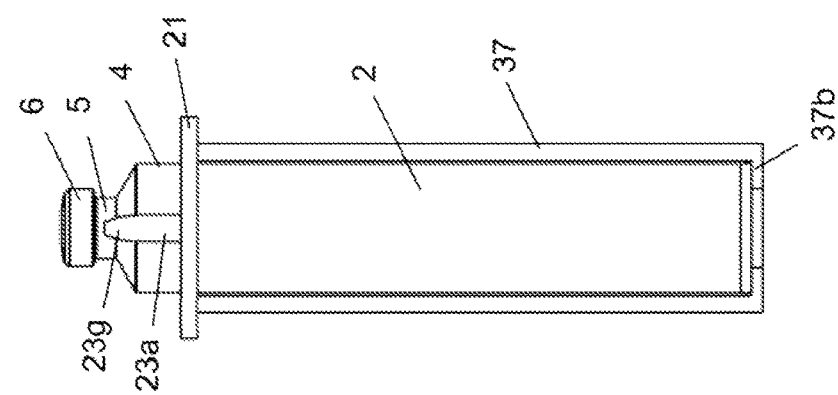
Fig. 6f
Fig. 6e
Fig. 6d

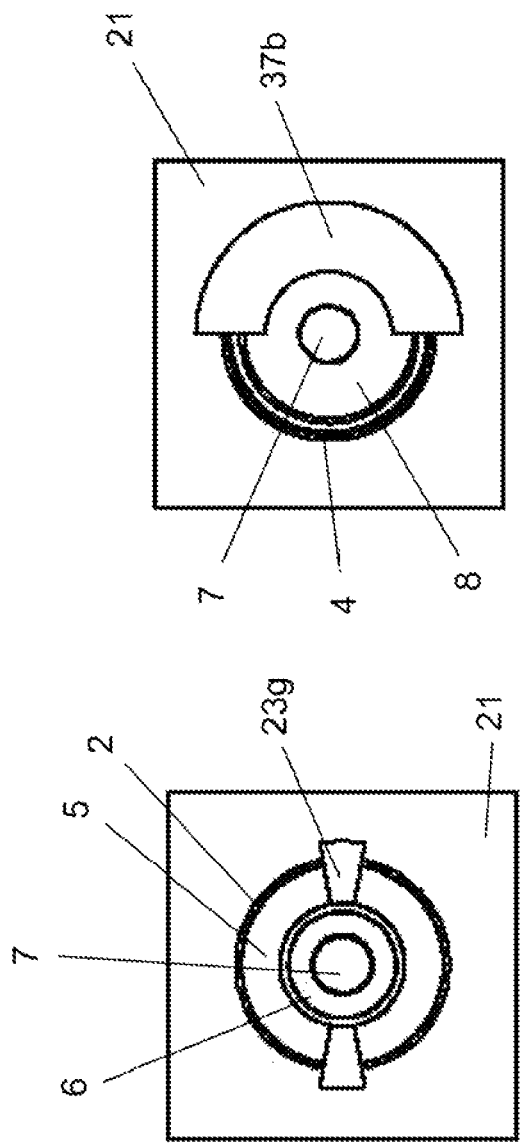

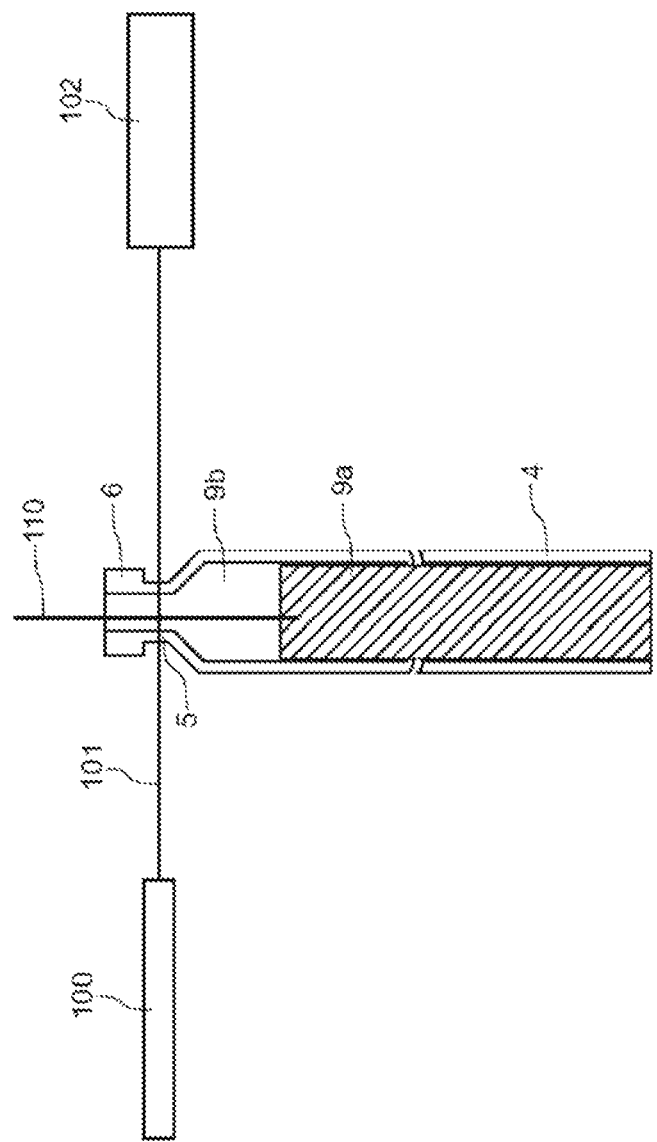

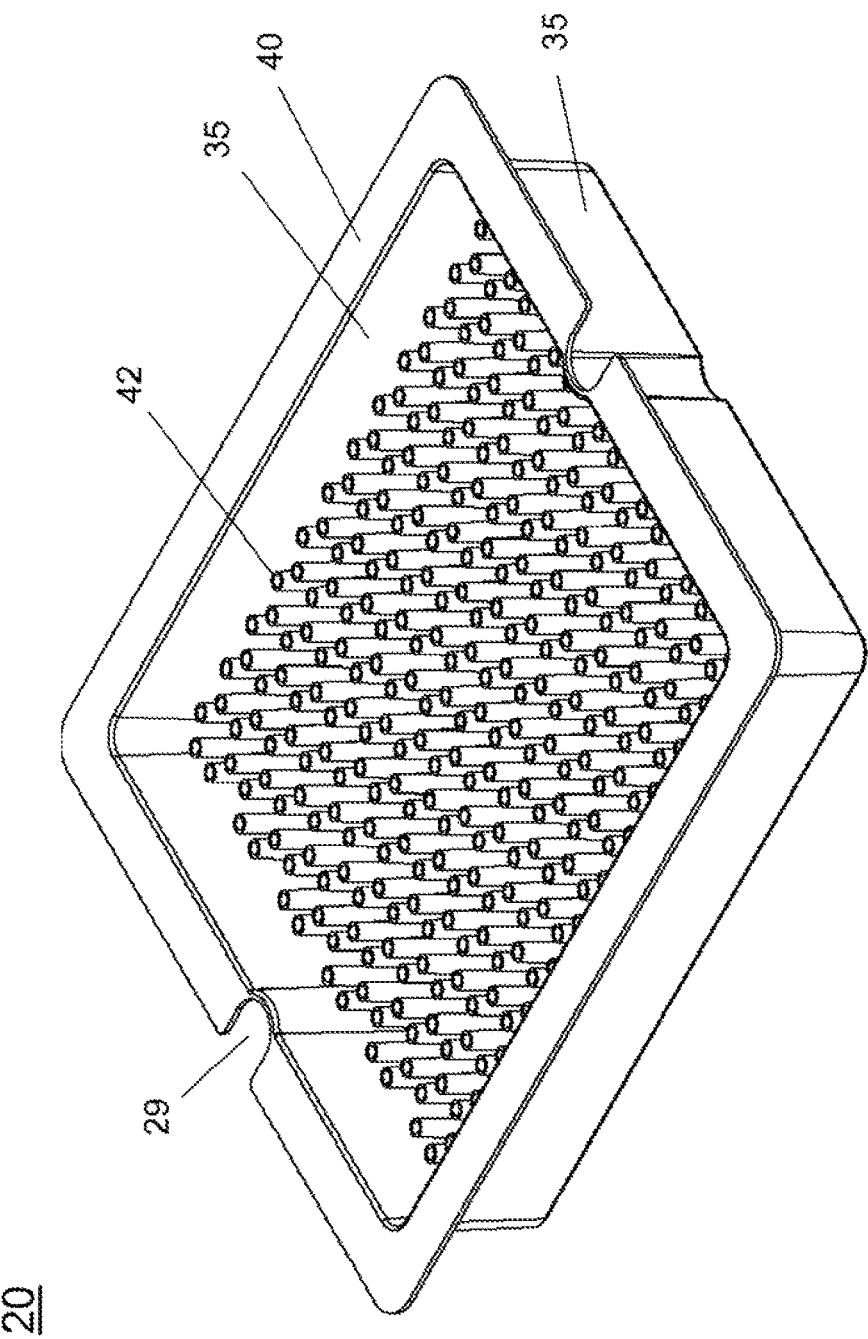

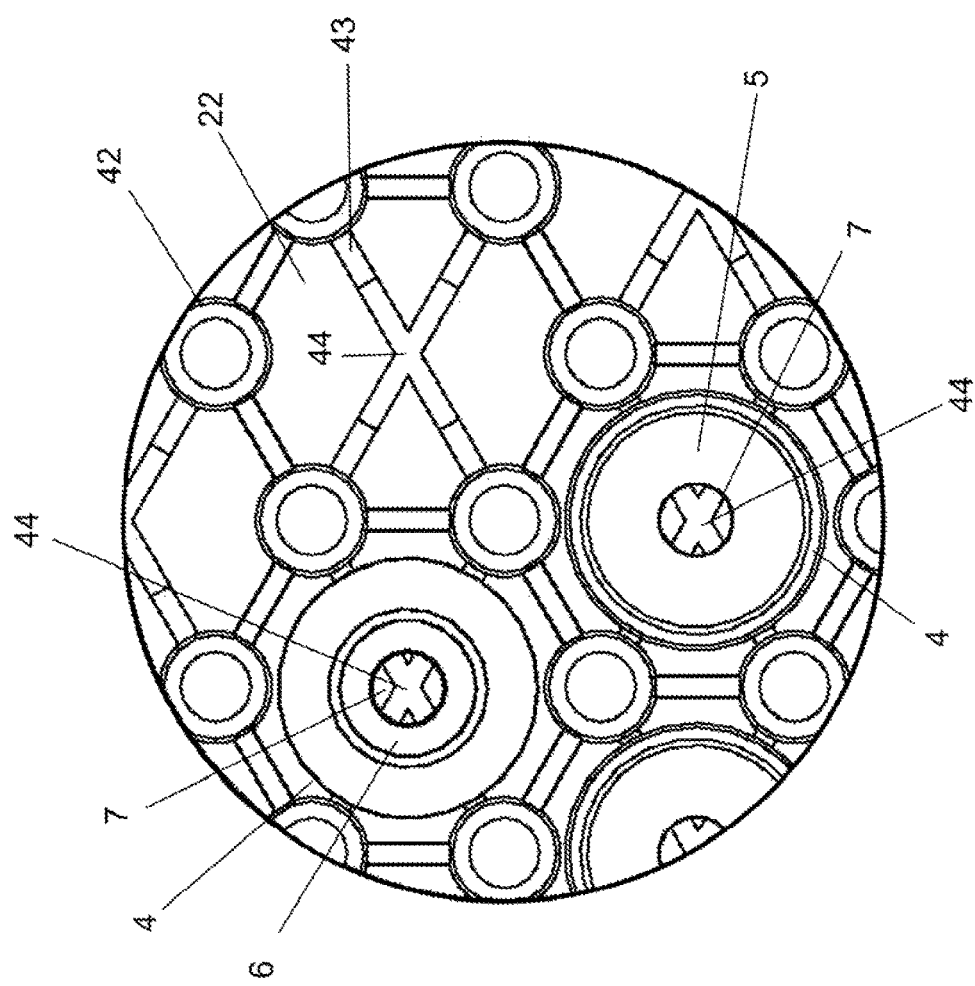

SUPPORTING STRUCTURE FOR CONCURRENTLY SUPPORTING A PLURALITY OF CONTAINERS FOR SUBSTANCES FOR MEDICAL, PHARMACEUTICAL OR COSMETIC APPLICATIONS

The present application claims the priority of German patent application no. 10 2013 112 167, "Supporting structure for concurrently supporting a plurality of containers for substances for medical, pharmaceutical or cosmetic applications as well as transport and packaging container comprising the same and process", filed on 5 Nov. 2013, the entire content of which is hereby incorporated by way of reference for the purpose of disclosure.

FIELD OF THE INVENTION

The present invention generally relates to the simultaneous supporting (holding) of a plurality of containers for the storage of substances for medical, pharmaceutical or cosmetic applications, in particular of vials, ampoules, syringes or dual-chamber syringes, carpoules (cartridges), dual-chamber cartridges or vartridges, and relates in particular to the simultaneous supporting of a plurality of such containers in a supporting structure in a simple and reliable manner and in such a manner that the containers, while they are supported by the supporting structure, can be processed in a filling apparatus or in processing plants or can be processed further, particularly in a sterile tunnel, in a filling apparatus for liquid medical or pharmaceutical agents or in a freeze-dryer for this purpose. The present invention further relates to a transport and/or packaging container comprising at least one such supporting structure and to a process for the treatment or processing of such containers.

BACKGROUND OF THE INVENTION

Medication containers, for example vials, ampoules or carpoules, are widely used as containers for preservation and storage of medical, pharmaceutical or cosmetic preparations to be administered in a liquid form, in particular in pre-dosed amounts. These generally have a cylindrical shape, can be made of plastic or glass and are available in large quantities at low costs. In order to fill the containers under sterile conditions as efficiently as possible concepts are increasingly used according to which the containers are already packaged in a transport or packaging container at the manufacturer of the containers under sterile conditions, which are then unpacked and further processed at a pharmaceutical company under sterile conditions, in particular in a so-called sterile tunnel.

For this purpose, various transport and packaging containers are known from the prior art, in which a plurality of medication containers are concurrently arranged in a regular. This has advantages in the automated further processing of the containers because the containers can be transferred to processing stations, for example to processing machines, robots or the like, at controlled positions and in a predetermined arrangement. For the transfer to a processing station it is just required to properly position and open the transport and packaging container. The downstream processing station will then know at what position and in what arrangement the containers to be processed further are arranged.

Such a transport and packaging container and a corresponding packaging concept is for example disclosed in U.S. Pat. No. 8,118,167 B2. The further processing of the containers is, however, always performed in such a manner that the supporting structure will be removed from the transport and packaging container, that the containers will be removed from the supporting structure and isolated and then individually placed on a conveyor, in particular a conveyor belt, and passed to the processing stations individually for the further processing. This limits the speed of processing that can be achieved. Particularly in the isolation of the containers by means of cell wheels or the like, it always occurs that individual containers abut uncontrolled, which results in an undesired abrasion and subsequently in a contamination of the interior volume of the containers or of the processing station and in an impairment of the outer appearance of the containers which is undesirable.

U.S. Pat. No. 8,100,263 B2 discloses a portable transport and packaging container that can be packaged in a sterile manner, in which a plate-shaped supporting structure can be inserted which supports a plurality of medication containers in a regular arrangement. However, the medication containers cannot be processed further while they are accommodated in the transport or packaging container or while they are supported in the supporting structure, but must be isolated first in the conventional manner and handed over to downstream processing stations.

Further similar transport and packaging containers and supporting structures are disclosed in WO 2011/135085 A1 and WO 2009/015862 A1. However, for the further processing the medication containers always need to be isolated. A further processing of batches of medication containers, while they are accommodated in a plate-shaped supporting structure as outlined above, is not possible.

SUMMARY OF THE INVENTION

The object of the present invention is to further enhance the supporting of containers used for the storage of substances for medical, pharmaceutical or cosmetic applications, so that the containers can be supported easily and reliably in accordance with the specific conditions during their treatment of processing and can be packaged sterile, can be unpackaged and processed further. According to a further aspect of the present invention there is to be provided a corresponding transport and packaging container comprising at least one such supporting structure and a corresponding process for the treatment or processing of containers.

Thus, there is provided a supporting structure for concurrently supporting a plurality of containers of a predetermined length, which are used for the storage of substances for medical, pharmaceutical or cosmetic applications or contain such substances, comprising a carrier (supporting structure) having a plurality of supporting means to support the containers, optionally, at least in a first position or in a second position on the carrier, wherein the containers are supported on the carrier in said first position with a first orientation (e.g. upright) and in said second position with a second orientation that is identical to said first orientation (e.g. also upright) or that is opposite to said first orientation (e.g. upside-down). According to the present invention the carrier is matched to the lengths of the containers in such a manner that the upper ends of the containers are arranged in said first position at the same distance to the upper rim of the carrier or to the upper rim of a frame used for supporting the carrier as the lower ends of the containers in the second position, and that the upper ends and/or lower ends of the containers are accessible for a further processing of the containers, while they are supported on the carrier.

Thus, there is no need to adjust the heights of processing stations where the containers are treated or processed further, regardless of whether the containers are supported on the carrier in the first position (e.g. upright) or in the second position (e.g. upside-down), because the upper ends and lower ends of the containers are disposed on the same height level in both positions (orientations) of the containers. According to the invention this facilitates the treatment and processing of containers considerably because the effort in terms of adjustment, control and automation can be considerably simplified.

The term "at the same distance" in the sense of the present application shall, or course, take into account unavoidable tolerances of the lengths of the containers. On the other hand, according to further embodiments also tolerances shall be taken into account that are caused by a different supporting of the upper ends and lower ends of the containers on the supporting structure and that are preferably at maximum of the order of the axial length of a constricted upper neck portion of the containers to be supported or that is slightly larger, in comparison to the total length of the containers to be supported, than this axial length, e.g. by less than 20%, preferably by less than 10% of the axial length of the constricted neck portion.

According to a further embodiment the carrier comprises a plurality of apertures, a plurality of supporting means, preferably two supporting means, being associated to said apertures, for supporting said containers, in particular by a positive-fit or by friction. Here, the containers are supported by the supporting means on the carrier preferably in such a manner that they extend through the apertures of the carrier, that the upper ends of the containers protrude beyond an upper rim of the carrier and/or that the lower ends of the containers protrude beyond a lower rim of the carrier.

According to a further embodiment the containers are supported on the carrier or retained in axial direction on the carrier in the first position and in the second position so that they are reliably supported on the carrier if its orientation is reversed.

According to a further embodiment the carrier, which is preferably planar and in particular rectangular, comprises at least two supporting tongues as supporting means that are provided on the edge of a respective aperture and protrude from an upper surface of the carrier to support the respective container in said aperture. Here, the supporting tongues are configured such that they are elastically pivoted away or flapped away during insertion of the containers into the apertures, and further such that the supporting tongues are matched to the containers such that the containers are supported by the supporting tongues with a radial clearance. The radial clearance enables that containers with different radial tolerances and/or outer dimensions can be supported reliably by the same carrier. Conveniently, the radial clearance is designed and matched to the outer contour or to the outer dimension of the container in such a manner that all supporting tongues are never at the same in contact with the constricted neck portion at the upper end of the container, in particular of the vial. At the same time the radial clearance also prevents an undesired tension or even bulging of the carrier when supporting containers having different radial tolerances and/or different outer dimensions, which offers considerable advantages in particular in the case of the concurrent processing of a plurality of containers, while these are supported by the carrier, e.g. during freeze-drying and processing at very low temperatures.

According to a further embodiment the supporting tongues are formed sufficiently resilient or are supported resiliently, so that the containers can be inserted in axial direction, i.e. in the direction of the longitudinal axes of the containers and perpendicular to the plane of the carrier, from the upper side or underside of the carrier into the apertures or receptacles, in particular under elastic deformation of the supporting tongues, e.g. under bending of the same. Thus, loading the carrier with containers can be easily automated, which is further enhanced by a regular arrangement of the apertures or receptacles, preferably by a regular arrangement of the apertures or receptacles in a two-dimensional matrix.

The underside of an expanded upper rim of the container has turned out to be a preferred position where the containers are held or supported by the supporting tongues, such as the so-called rolled edge or shoulder that is usually provided in the case of vials. In this region a supporting area is available having a sufficient extent in the radial direction of the apertures or receptacles for holding or supporting the containers, in order to easily implement the afore-mentioned radial clearance when supporting the containers.

Because the containers can be lifted or displaced, e.g. rotated, with low efforts in the apertures or receptacles of the carrier, according to the invention the containers can be easily processed while they are within the carrier and are supported or at least guided by it. This kind of supporting turned out to be of particular advantage e.g. during sealing of the containers by crimping a metal lid. The processes required for this purpose can be performed on the metal lid while the containers are supported or at least guided in the apertures or receptacles of the carrier. This kind of supporting turned out to be of particular advantage for the processing of containers, while the containers are supported or accommodated in the carrier. E.g. the carrier together with the containers supported can be placed in a freeze-dryer or freeze-drying cabinet. Because of the supporting of the containers with a certain clearance in the carriers it can be ensured that the bottoms of all containers evenly rest on a cooling base, e.g. a cooling finger of the freeze-diver or freeze-drying cabinet. Or the containers can be lifted and handled for the processing without much effort while being in the apertures or receptacles of the carrier.

According to a further preferred embodiment the supporting tongues are resilient supporting tongues, but have a sufficient elasticity to be pivoted away or folded away resiliently and to a sufficient extent upon insertion of the containers into the apertures or receptacles to give free the path into the apertures or receptacles. This can be accomplished easily by a suitable dimensioning, choice of materials and configuration of the strength of the material of the supporting tongues. Preferably, the supporting tongues are thus formed of a plastic material.

According to a further embodiment the supporting tongues are biased resiliently towards a retaining position, preferably by a resilient restoring member such as a restoring spring or a plastic plate or an elastic plastic structure, which cooperates with the associated supporting tongue suitably and is disposed or formed on the upper surface of the carrier.

According to a further embodiment the supporting tongues are matched to the containers such that the containers rest loosely with an expanded rim that is formed at an upper end of the container on the upper sides of the supporting tongues, in particular with the afore-mentioned rolled edge. Thus, the containers can be removed upward out of the apertures or receptacles without a significant resistance.

According to a further embodiment the supporting tongues embrace the expanded rim in such a manner that the containers are supported on the supporting tongues with a radial clearance or both with a radial clearance and an axial clearance. In this manner the containers can be retained in the apertures in axial direction and in a loose-proof manner so that the carrier can be turned over without problems. For removing the containers out of the apertures, the supporting tongues only need to be pivoted or flapped back again in the same manner as for inserting the containers.

According to a further embodiment the apertures are at least partially delimited by a sidewall or by one or more pins on one side of the carrier, namely on the upper side or the underside of the carrier, for preventing a collision of containers in directly adjacent apertures or receptacles. Here, most preferably the side walls or pins are formed in such a manner that the containers are freely accessible from this side of the carrier. i.e. from the upper side or from the lower side. Here, the side walls of adjacent apertures or receptacles of the carrier can also be connected with each other, which advantageously contributes to a further stiffening of the carrier. Preferably, the side walls are integral with the carrier, which can be implemented easily using a plastic injection molding technique.

The bottoms or lower ends of the containers accommodated in the apertures preferably protrude from the ends of the side walls so that the bottoms or lower ends of the containers are freely accessibly from the underside or upper side of the carrier. This makes it possible that the containers can be processed while they are supported on the carrier in the apertures or receptacles, as outlined below.

According to a further embodiment the carrier is formed in two parts and further comprises a frame, on which the carrier can be supported in a respective opposite orientation, for supporting the containers on the carrier in the first position or in the second position. Members that interact with each other positively can be provided on the frame and on the carrier for defining a different height difference between the frame and the carrier in the respective orientation.

For embodiments where the carrier is accommodated directly in a transport and packaging container, the height level of the carrier in the respective orientation can be defined in a corresponding manner also by members that interact with each other positively and that are provided on the carrier and on the inner side of the transport and packaging container.

A further aspect of the present invention relates to a transport and packaging container comprising at least one supporting structure as outlined above and disclosed in more detail hereinafter.

Preferably, the containers respectively do not protrude beyond an upper rim and/or beyond a lower rim, respectively, of the transport and packaging container when the containers are supported on the carrier in the first position or in the second position so that the transport and packaging container can be sealed under sterile conditions for a transport of the containers, e.g. by means of a sealing foil which is bonded to the upper rim and/or lower rim of the transport and packaging container.

A further aspect of the present invention relates to a process for the treatment or processing of containers used for the storage of substances for medical, pharmaceutical or cosmetic applications or containing such substances, wherein the containers are open at least at one end and wherein a supporting structure, as disclosed herein, and/or a transport and packaging container, as disclosed herein, is used.

In the process the containers are conveyed by a conveying device automated past processing stations or are passed through them, while the containers are supported by a carrier in a predetermined configuration as outlined above. The containers are treated or processed while they are supported by the carrier. According to the invention the containers are optionally supported on the carrier in a first position or in a second position, wherein the containers are supported on the carrier in the first position with a first orientation and in a second position with a second orientation that is identical or opposite to said first orientation, in particular upright in the first position and upside-down in the second position. According to the invention the upper ends of the containers are arranged in the first position at the same distance to the upper rim of the carrier or to the upper rim of a frame used for supporting the carrier as the lower ends of the containers in the second position, wherein for the treatment or processing the containers are affected via their upper ends and/or their lower ends, while the containers are supported on the carrier.

The treatment or processing of the containers can in particular be a cleaning of the containers and/or a weighing of the containers and/or a filling of the containers and/or a sealing of the containers with stoppers or caps and/or a crimping of metal caps onto the containers.

According to a further embodiment the carrier can be formed in two parts and can comprise a frame, wherein the carrier is supported on said frame optionally in one of two opposite orientations, for supporting the containers on the carrier in the first position or in the second position for said treatment or processing.

According to a further embodiment of the process the treatment or processing of the containers can comprise a step for measuring filling capacities of the containers, where the containers are supported on the carrier in such a manner that a laser beam respectively propagates through a constricted neck portion of the containers and the laser beam is detected using a sensor, wherein the respective filling capacities of the containers, in particular a filling level of the containers, is determined on the basis of a measurement signal of the sensor.

A further aspect of the present invention relates to a process for sealing a container having at least one open end with a stopper, comprising the steps of: disposing a sealing member on an end of the container to seal said end of said container against the environment; inserting the stopper in a compressed state by means of a gripper into said end of the container; applying a vacuum to said end of the container via an annular gap between the gripper and an inner surface of the container; and releasing the stopper until it rests against the inner surface of the container, to seal said end of the container against the environment. Because the stopper is inserted into the open end of the container in a compressed state and because the inner volume of the container is sealed by a sealing member against the environment, an appropriate vacuum can be applied easily to the inner volume of the container to withdraw air or gases out of the inner volume by suction, before the stopper seals the end.

According to a further embodiment of the process the gripper comprises a cylinder having an outer diameter that is smaller than the inner diameter at said end of the container, wherein said step of inserting the stopper in a compressed state by means of a gripper into said end of the container further comprises: compressing the stopper by inserting the stopper into said cylinder; displacing the cylinder together with the gripper for inserting the stopper into said end of the container: applying a pressure to the sealing member for sealing said end of the container against the environment: and pushing the stopper out of the cylinder further into said end of the container and towards the surface of the liquid that is stored in the container. Here, the cylinder serves as a means for delimiting and guiding the stopper and the gripper for reliably delimiting an annular gap between the outer wall of the cylinder and the inner wall of the container.

According to a further embodiment of the process the sealing member is a part of the bottom of a carrier or of a supporting structure as outlined above, wherein the containers are disposed on the bottom of the carrier or of the supporting structure such that the ends of the containers are aligned with the apertures formed in the bottom and that the stoppers are inserted into the ends of the containers via said apertures. Here, the stopper can be accommodated in a compressed state in the cylinder upon insertion into the apertures. Thus, the stoppers can be positioned in particular at times when the containers rest in their normal transport position in a carrier, as disclosed herein, e.g. when the carrier is removed out of a transport and packaging container, as disclosed herein. Thus, according to the invention the stoppers can be inserted into the upper ends of the containers, while they are supported in a carrier (nest). Particularly, the containers can be cylinder ampoules or cartridges (carpoules) that are supported in a carrier, which is accommodated under sterile conditions and transported in a transport and packaging container, wherein the transport and packaging container is opened at a pharmaceutical company and the cylinder ampoules or cartridges are then filled and sealed by placing a stopper in the manner disclosed herein, while the cylinder ampoules or cartridges are supported in the carrier.

In this process the sealing member may also be fed as a separate member, in particular as a plate comprising a plurality of annular sealing members that are connected with each other via webs of the like.

OVERVIEW ON DRAWINGS

Figure 5A:
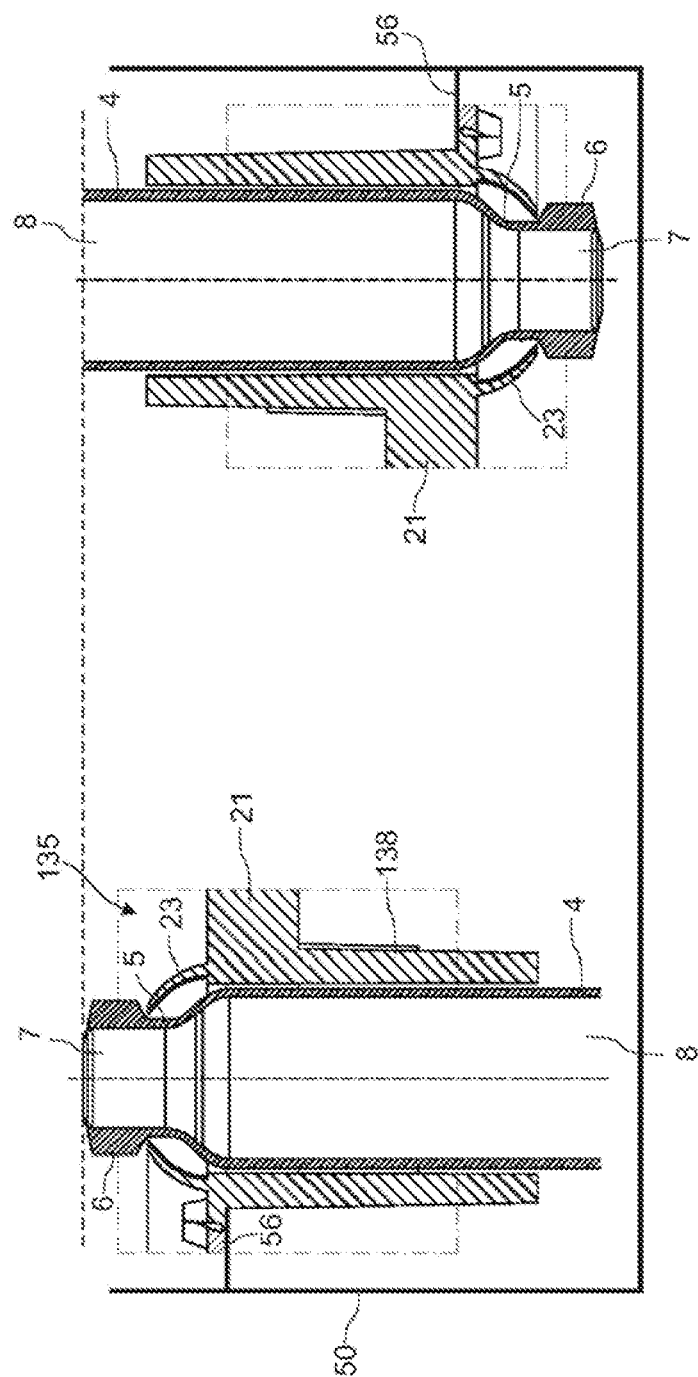
Figure 5B:
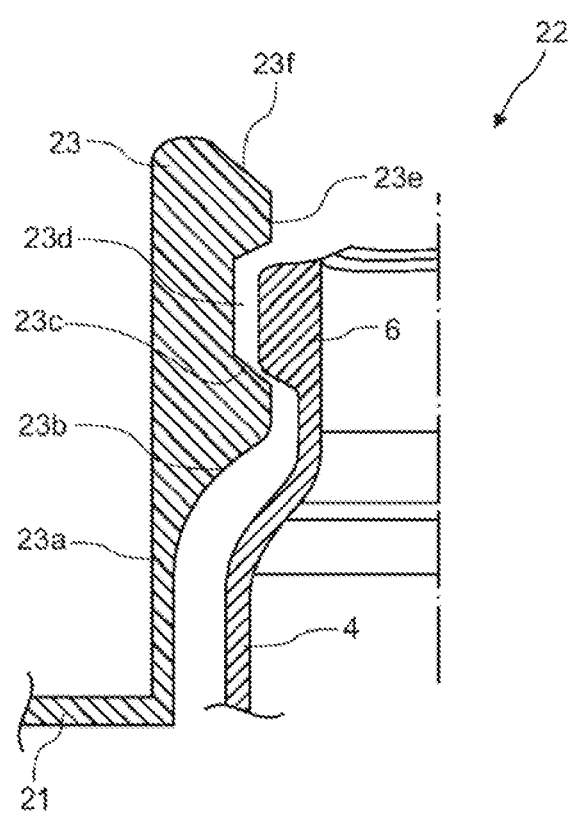
Figure 7B:
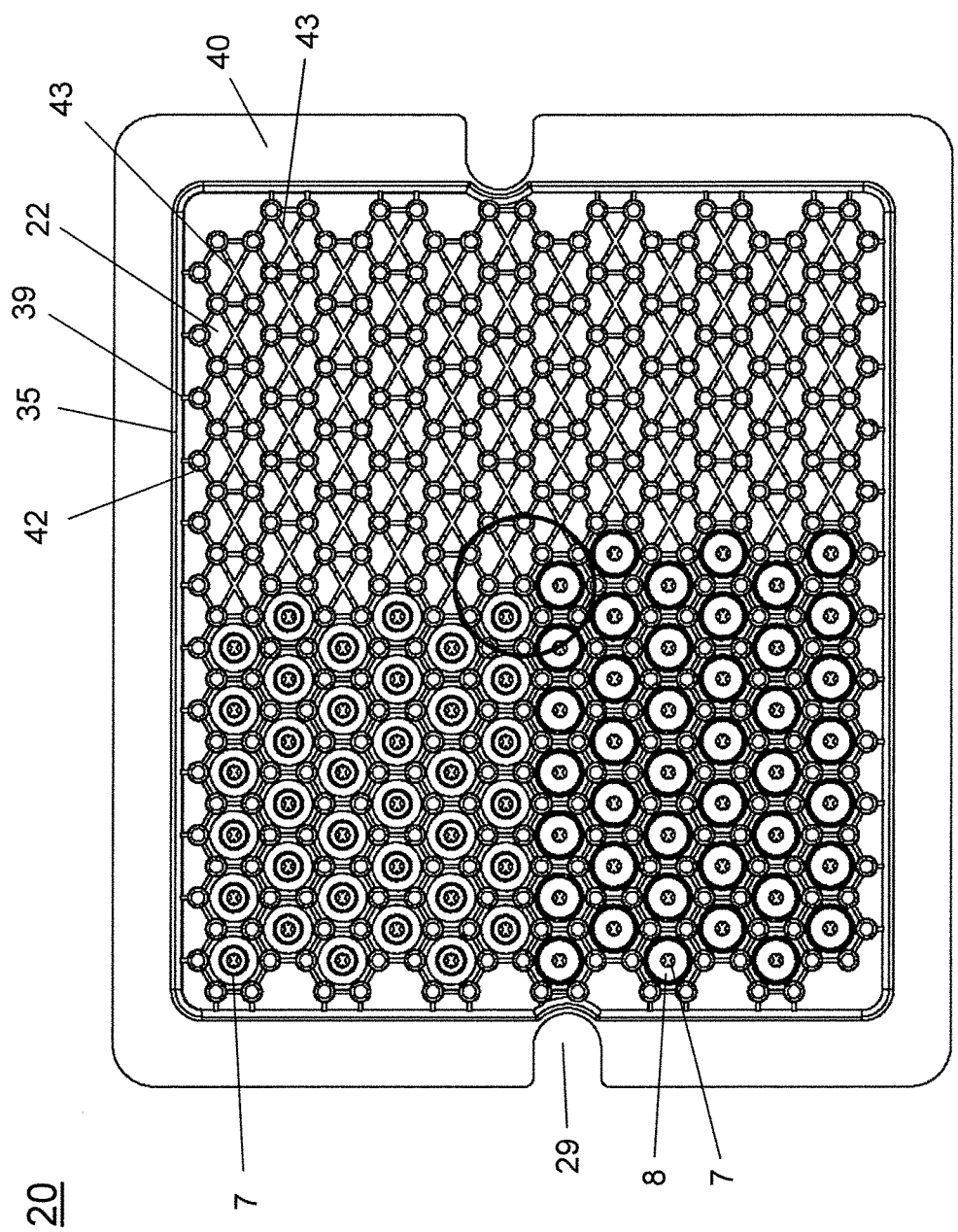
Figure 7D:
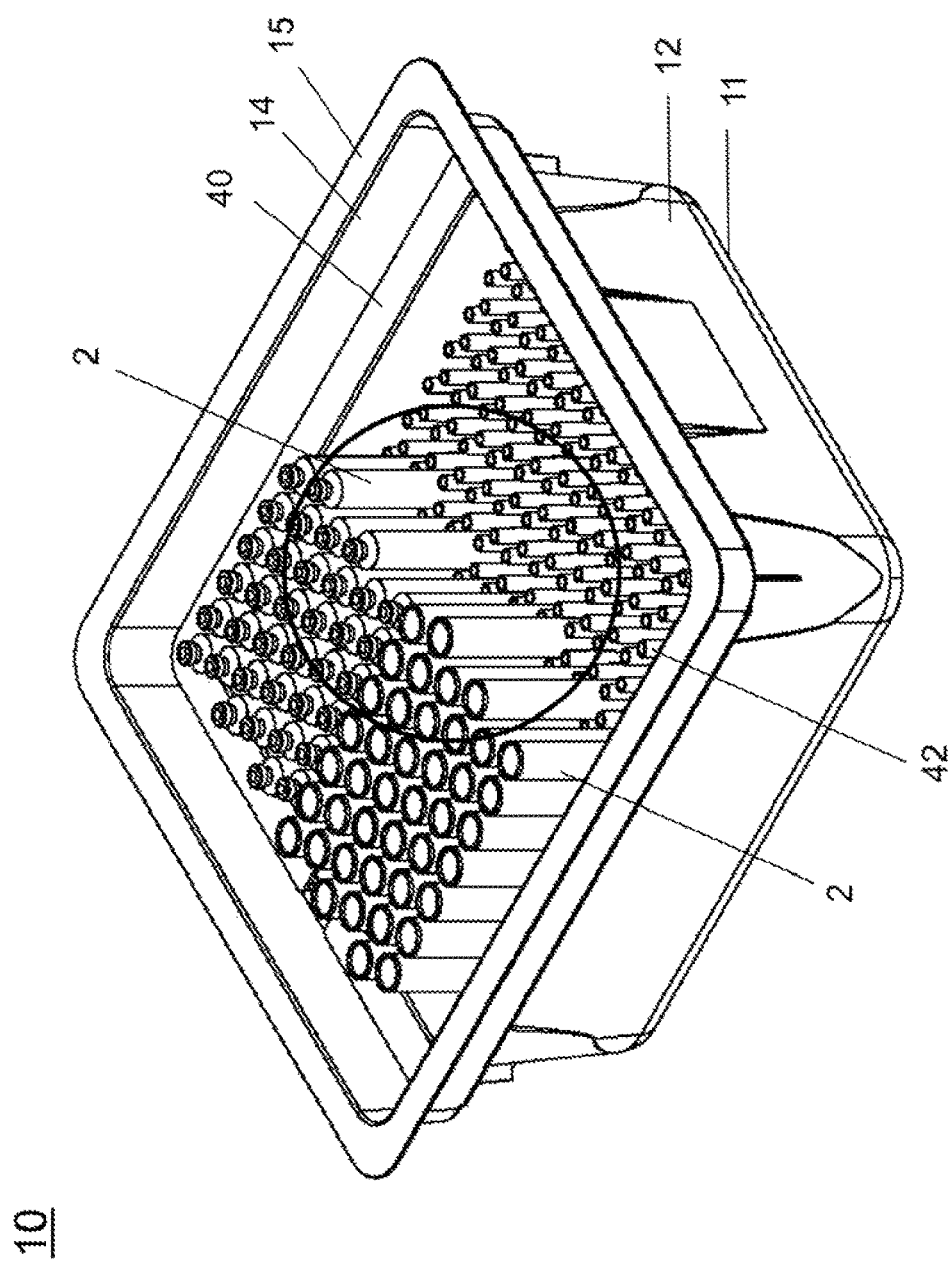
Figure 7E:
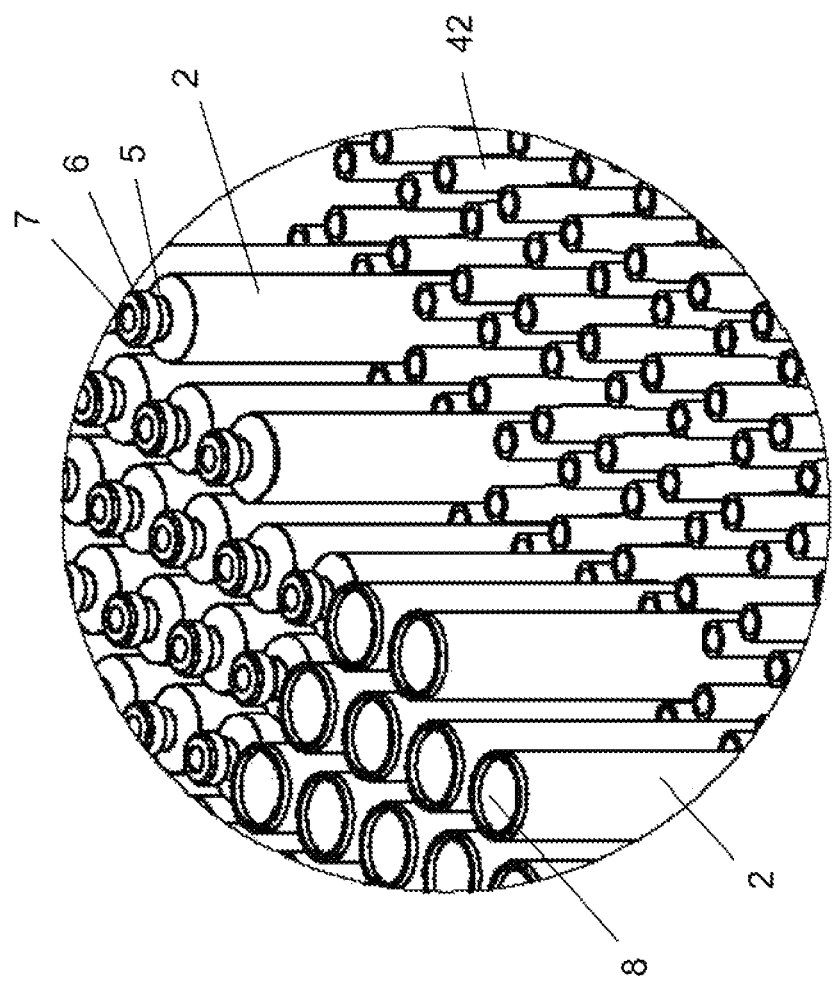
Figure 7F:
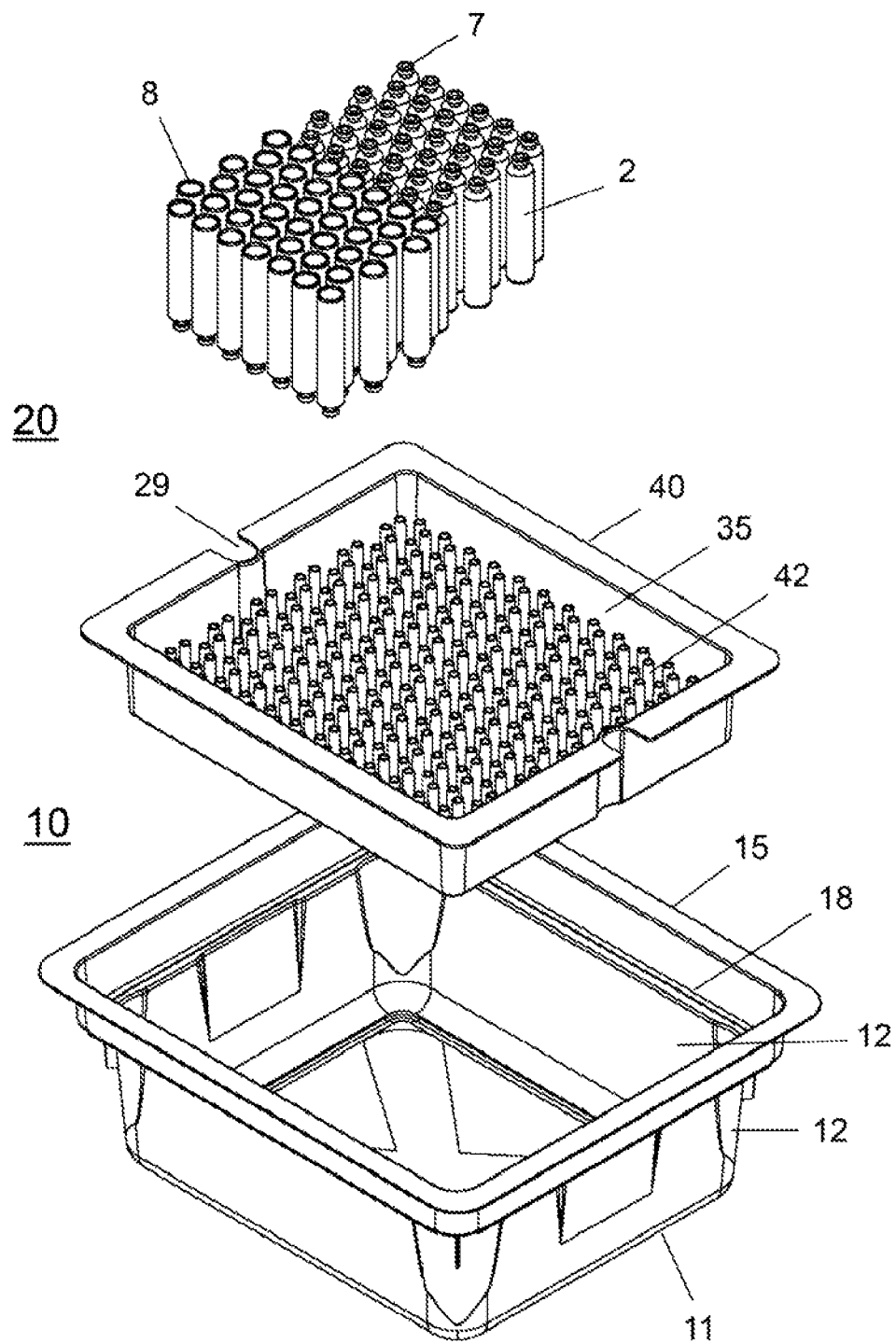
Figure 8A:
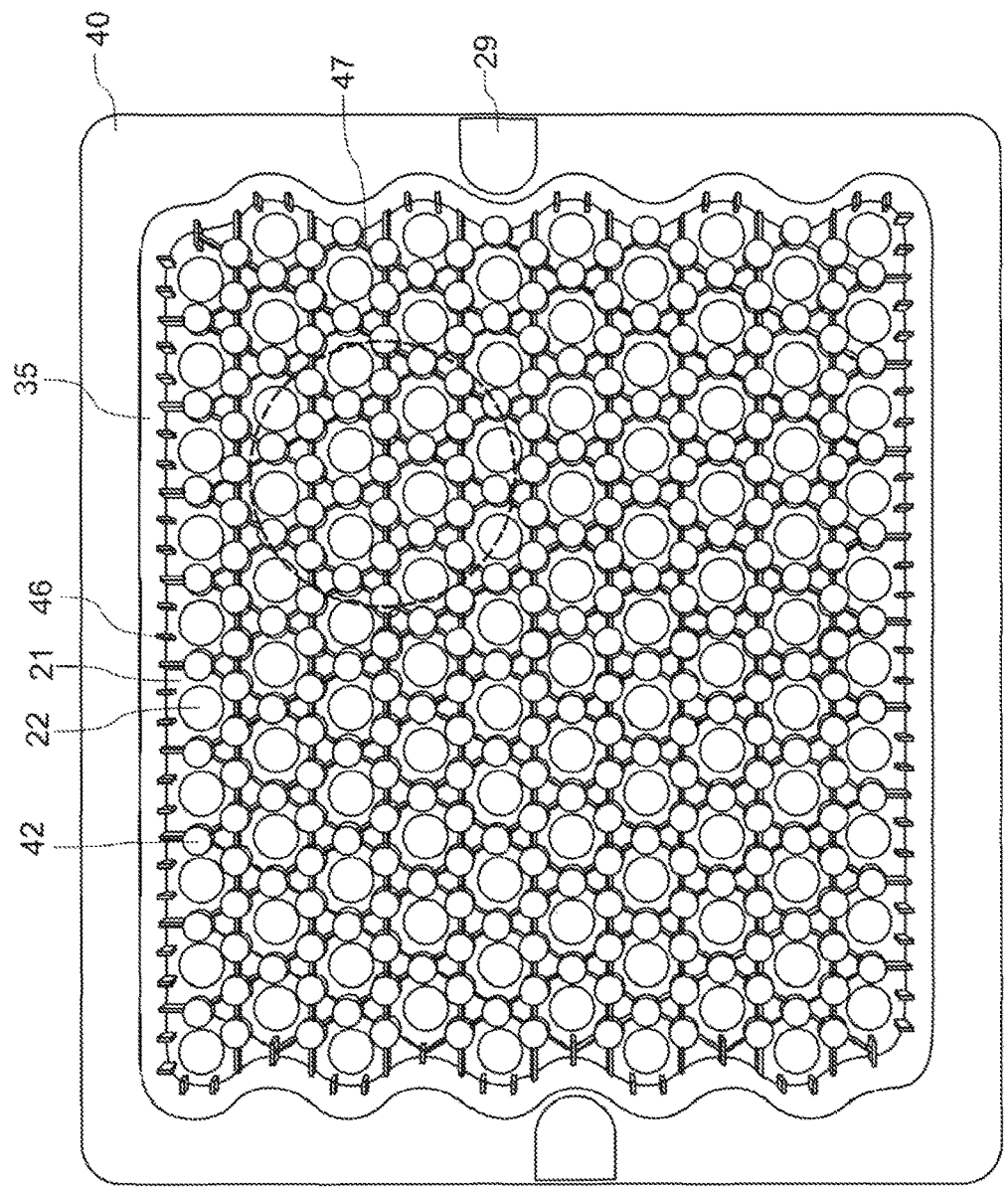
Figure 8B:
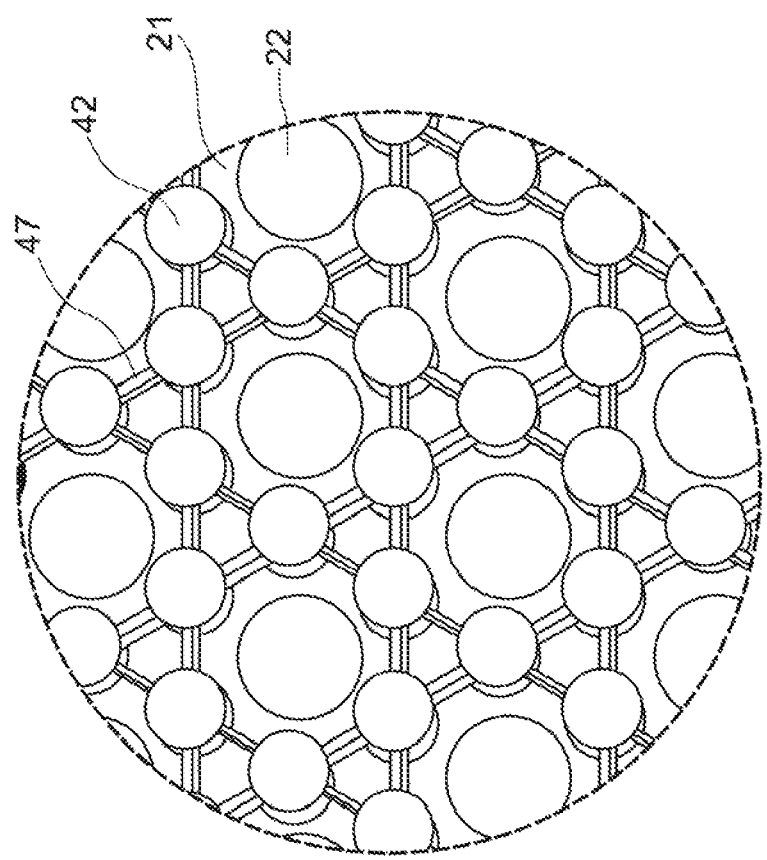
Figure 8E:
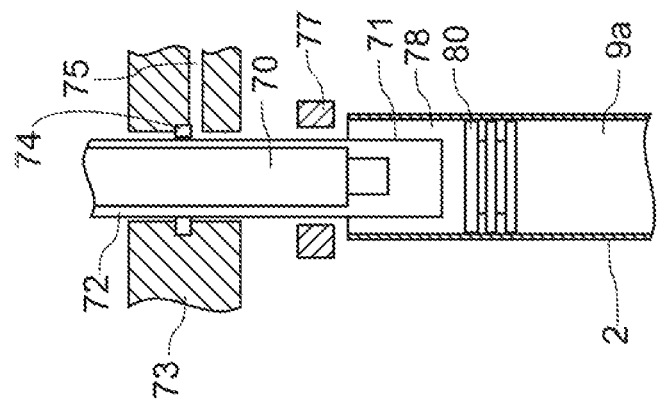
Figure 8D:
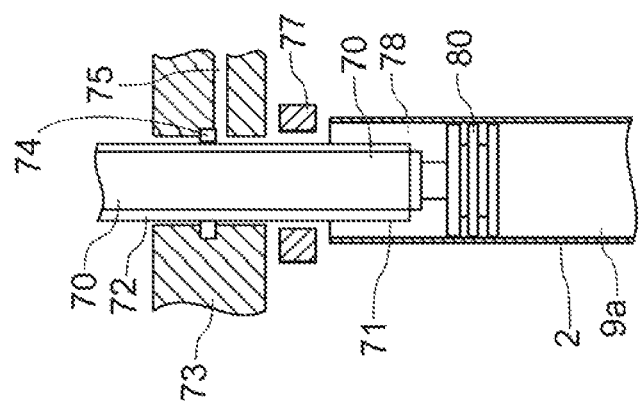
Figure 8C:
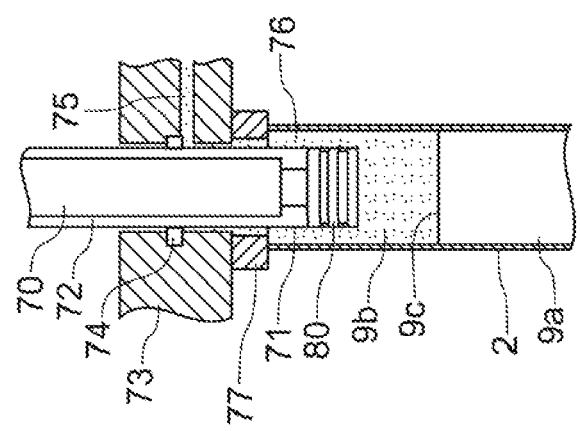
Figure 9A:
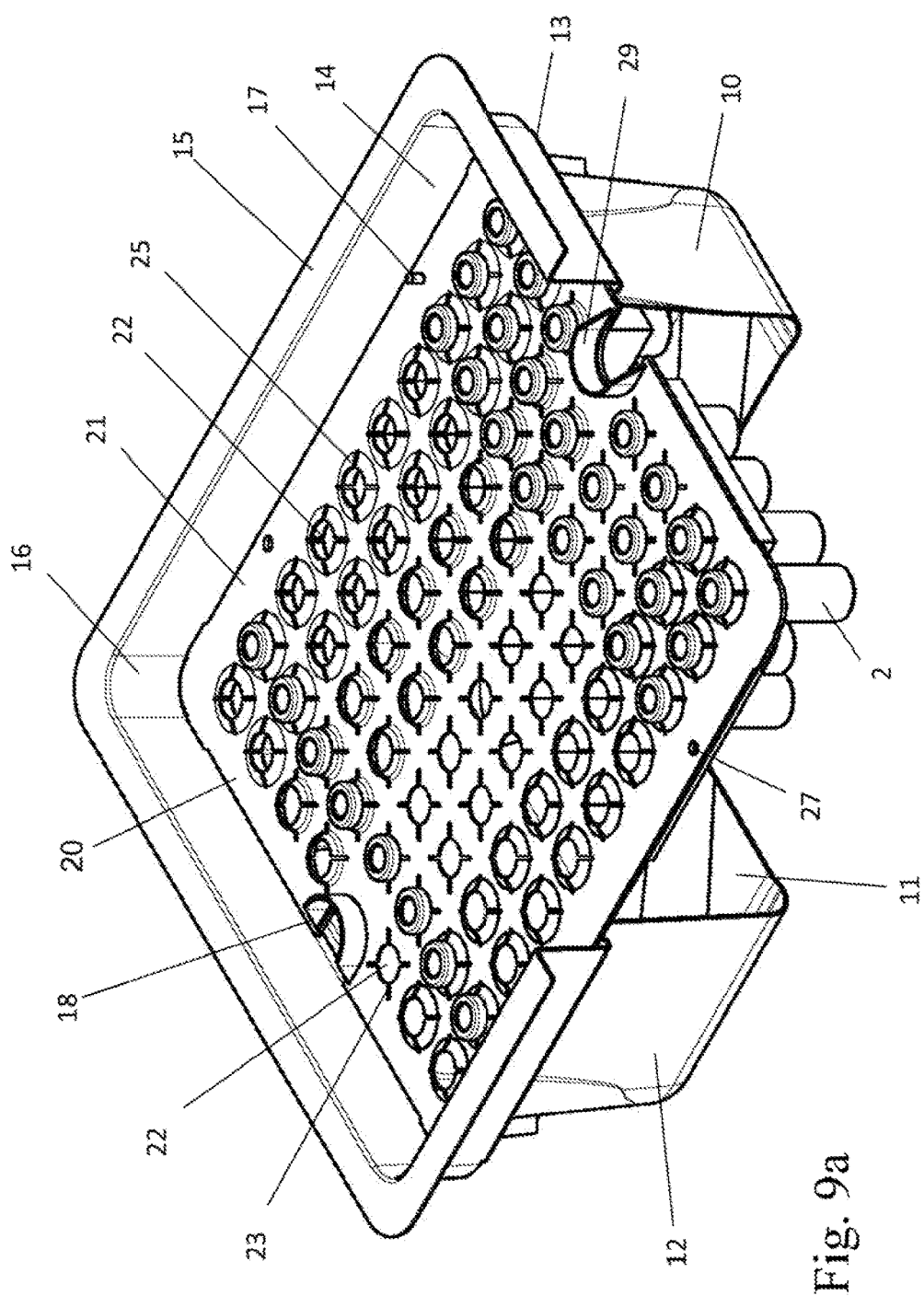
Figure 9B:
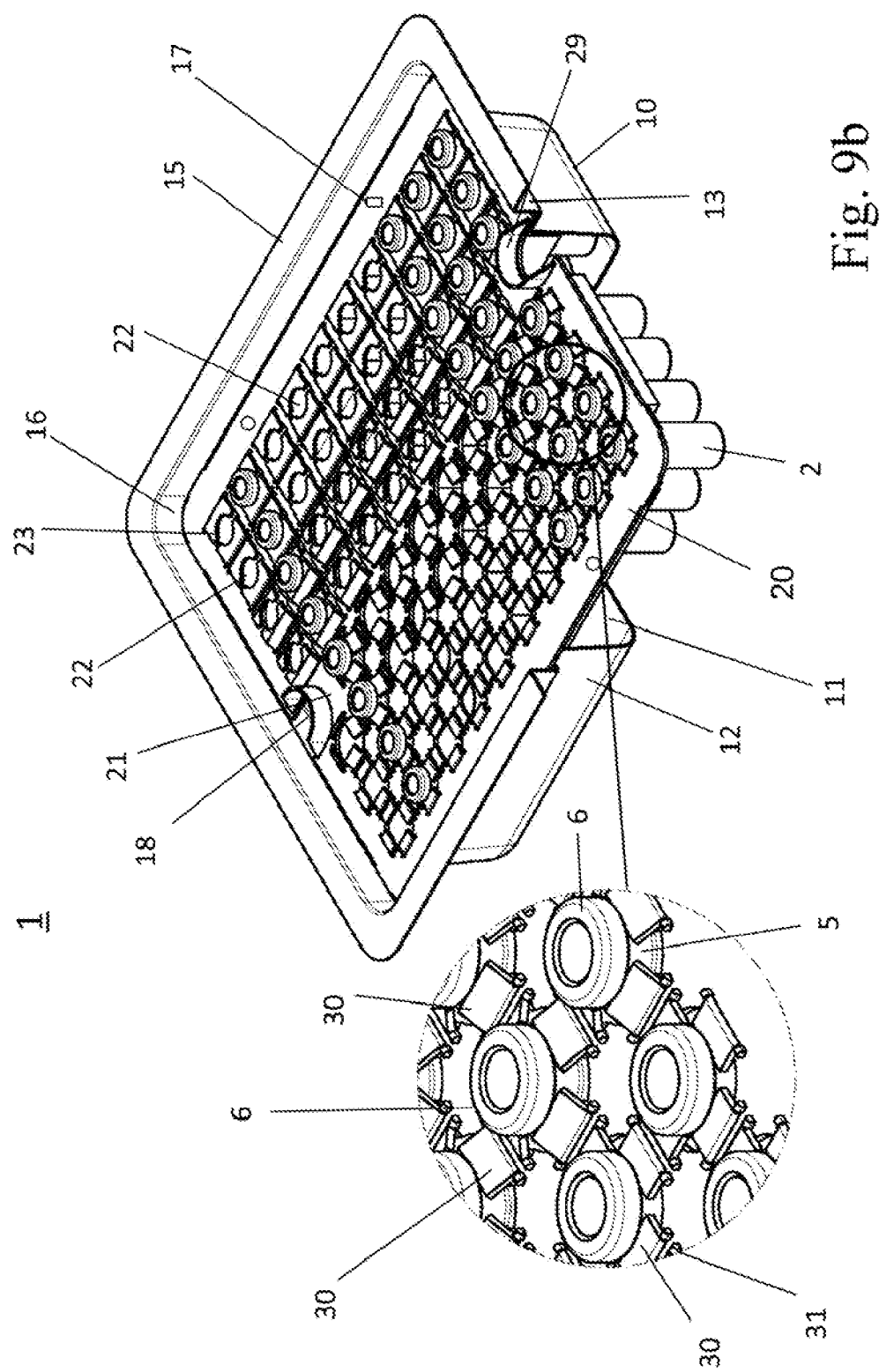
Figure 9C:
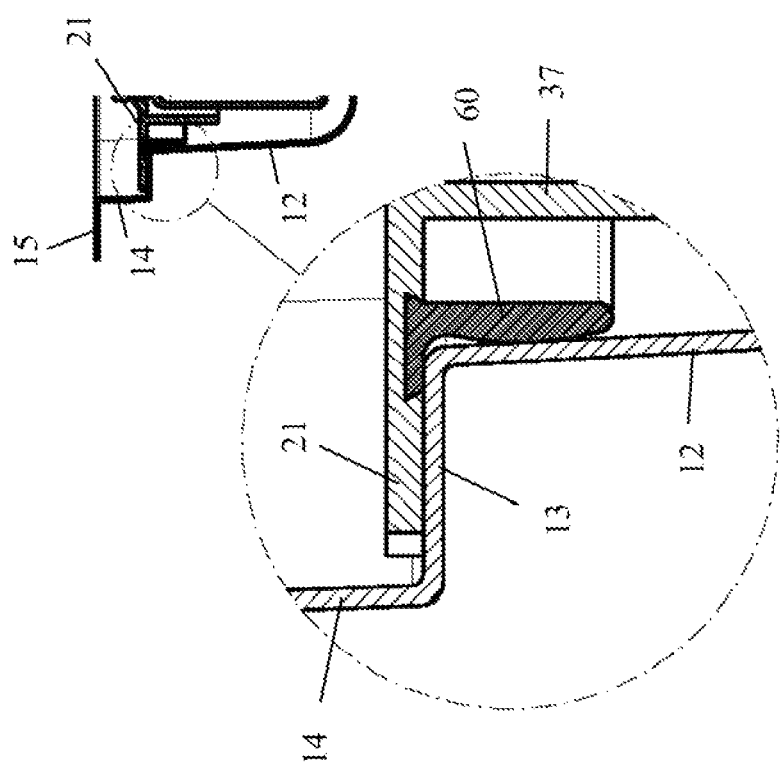

The invention will now be described by way of example and with reference to the accompanying drawings, from which further features, advantages and problems to be solved will become apparent. In the drawings:

FIG. 1 shows a container for storing substances for medical, pharmaceutical or cosmetic applications, which is embodied as a vial:

FIGS. 2*a* to 2*g* show the basis components of a two-part supporting structure according to a first embodiment of the present invention;

FIGS. 3*a* to 3*g* show the accommodation of such a supporting structure in a transport and packaging container according to the present invention;

FIGS. 3*h* and 3*i* show in comparative views the supporting structure according to FIGS. 2*a* to 2*g* in a first position and a second position of the containers:

FIGS. 4*a* to 4*j* show a supporting structure and a transport and packaging container according to a further embodiment of the present invention:

FIG. 4*k* shows in an exploded perspective view the transport and packaging container of FIGS. 3*a* to 3*g* with a supporting structure of FIGS. 2*a* to 2*g*;

FIG. 4*l* is a schematic diagram of a process for the concurrent treatment of processing of a plurality of containers according to the present invention;

FIGS. 5*a* and 5*b* show further examples for the supporting of a container at a carrier of a supporting structure according to the present invention;

FIGS. 6*a* to 6*h* show further examples for the supporting of a container at a carrier of a supporting structure according to the present invention;

FIG. 6*i* shows a process step in a method according to the present invention for determining the filling level or filling level of a container using a laser:

FIGS. 7*a* to 7*e* show a supporting structure according to a further embodiment of the present invention:

FIG. 7*f* shows in an exploded perspective view a transport and packaging container with the supporting structure according to FIGS. 7*a* to 7*e*;

FIGS. 8*a* and 8*b* show in a plan view and in a greatly enlarged partial view a supporting structure according to a further embodiment of the present invention;

FIGS. 8*c* to 8*e* show in schematic partial sectional views different stages of a process step for setting stoppers (stoppering) in cartridges in a process according to the present invention; and FIGS. 9*a* to 9*c* are perspective partial views of a transport and packaging container with three further embodiments of a supporting structure according to the present invention.

In the drawings, identical reference numerals designate identical or substantially equivalent elements or groups of elements.

DETAILED DESCRIPTION OF PREFERRED EMBODIMENTS

According to the present invention, a supporting structure as well as a transport and packaging container accommodating such a supporting structure are used, as described below, for concurrently supporting a plurality of containers for storage of substances for medical, pharmaceutical or cosmetic applications in an array configuration, preferably in a matrix configuration with regular intervals between the containers along two different directions in space, preferably along two mutually orthogonal directions in space or in regular rows that are offset relative to each other.

An example of such containers embodied as vials is schematically shown in FIG. 1 in a longitudinal sectional view. The vials have a cylindrical basic shape, having a cylindrical side wall 4 with—within tolerances—constant inner and outer diameters, which project vertically from a flat vial bottom 3, which merges in a constricted neck portion 5 of a relatively short axial length near the upper open end of the vial and then merges in an expanded upper rim 6 (also referred to as a rolled edge), which has a larger outer diameter than the associated neck portion 5 and is configured for connection to a closure member. As can be concluded from FIG. 1, the bottom edge of the rolled edge 6 can be slanted and may extend at an acute angle downward and toward the constricted neck portion 5. According to further embodiments, the bottom edge of the rolled edge 6 may also be flat and extend in radial direction substantially at a right angle relative to the constricted neck portion 5.

The neck portion 5 can be formed with smooth walls and without an external thread or may be provided with an external thread for screwing on a closure member. For example, a stopper (not shown) may be inserted in the inner bore of the neck portion 5 and the upper rim 6, whose upper end is connected with the upper rim 6 of the vial in a gas-tight manner and protected against the intrusion of contaminants into the vial, for example by crimping or beading a metal protective foil which is not shown. Such vials are radial symmetric and are made of a transparent or colored glass or of a suitable plastic material by blow molding or plastic injection molding techniques, and in general can be internally coated so that the material of the vial emits minimal impurities to the agent to be received.

Further examples of a medication container according to the present application are ampoules, carpoules (cartridges), syringes or injection containers. Ampoules or carpoules are containers for medication agents for usually parenteral administration (injection), for cosmetics and other agents and are usually cylindrical in shape with an extended tip (spear or head) and a flat bottom or also with two extended tips at both ends. These may be formed in particular as snap-off ampoules with an annular predetermined breaking point around the ampoule neck or as an OPC cartridge (One-Point-cut ampoule) having a breaking ring inscribed into the glass. Syringes or injection containers, also known as injection flasks, vials or reusable ampoules, are cylindrical containers of glass or plastic shaped similar to a bottle, usually having a relatively small nominal volume (e.g. 1 ml, 10 ml). They are sealed with a rubber stopper (plug) with septum (puncture rubber). For protecting the septum and fixing the rubber stopper an outer closure (beaded cap or cramp), often made from an aluminum sheet, is necessary. In a carpoule the liquid is stored in a cylinder, which is closed at one end by means of a thick rubber or plastic stopper. This acts as a piston when the content is pressed out using a carpoule syringe. At the other end the cylinder is closed only by means of a thin diaphragm, which is pierced from the rear end of the carpoule syringe (a cannula sharpened on both sides) in the application. Cylindrical ampoules are often used in dentistry for local anesthesia. Special cylindrical ampoules with a specially shaped front part (e.g. thread) are used for insulin therapy in insulin pens.

In the sense of the present invention, such containers are used for the storage of substances or agents for cosmetic, medical or pharmaceutical applications, which are to be stored in one or several components in solid or liquid form in the container. Especially in the case of glass containers storage periods can amount many years, notably depending on the hydrolytic resistance of the glass type used. While, in the following, cylindrical containers are disclosed, it should be noted that the containers, in the sense of the present invention, may also have a different profile, for example a square, rectangular or polygonal profile.

Inevitably such containers have tolerances due to the production which can be of the order of one or several tenths of a millimeter in particular for glass containers. To compensate for such manufacturing tolerances, while ensuring that all bottoms 3 or bottom ends of the containers can be disposed in a plane, according to the present invention the containers are fixed on a supporting structure as outlined in the following. This supporting of the containers is implemented either in the transition region between the constricted neck portion 5 and the expanded upper rim 6 or in the region of the constricted neck 5. As described hereinafter, a supporting member is disposed in the region of the constricted neck portion 5, which engages with the constricted neck portion 5 in a positive-fit manner or preferably accommodates the latter with a certain radial clearance to compensate for tolerances and different outer diameters of different types of containers. This supporting member may be part of a supporting means or is formed by the latter that is clipped into a carrier in accordance with embodiments of the invention, as described below, to form a supporting structure for concurrently supporting a plurality of containers in apertures or receptacles.

Figure 2A:
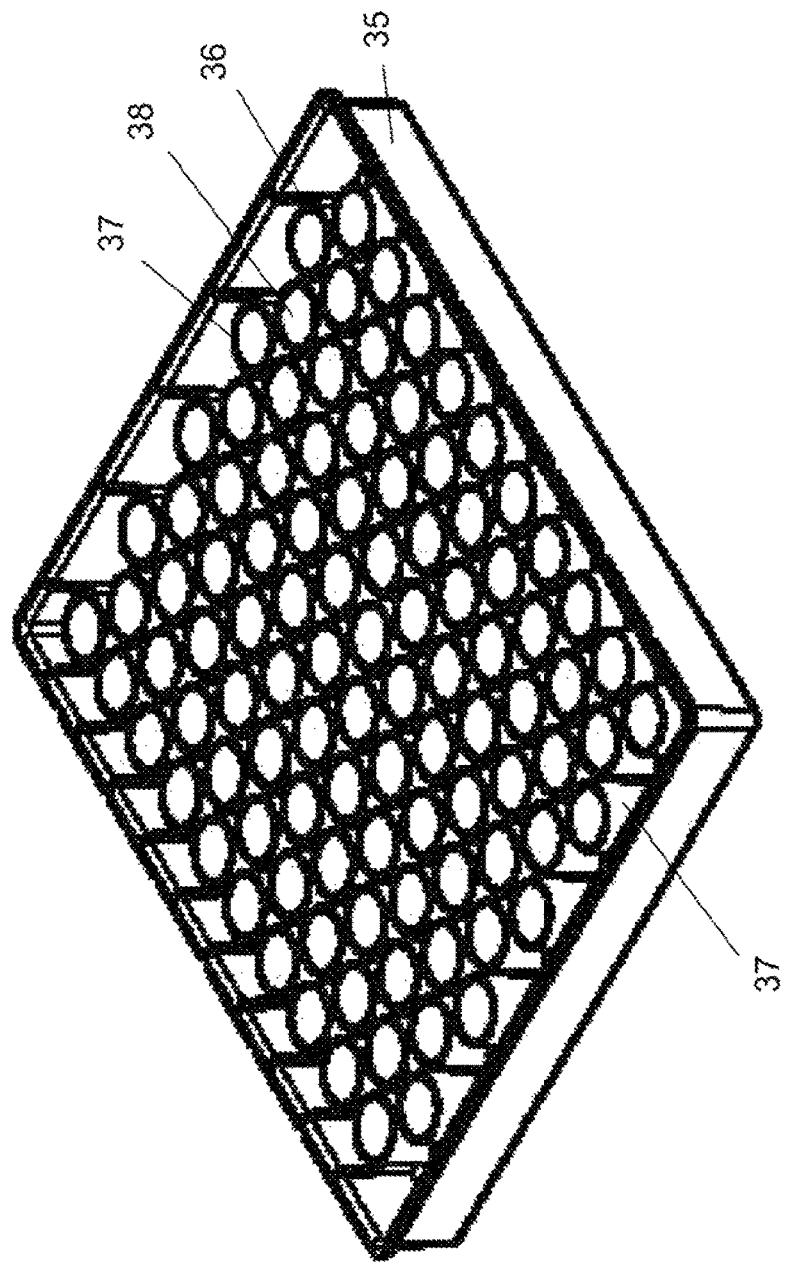

For concurrently supporting a plurality of containers according to a first embodiment of the present invention, as shown in FIGS. 2a to 2g, a planar rectangular carrier 20 (also referred to as a supporting structure in the present application) is provided, which is formed of a plastic, for example by punching or injection molding, and which comprises a plurality of apertures 22 for receiving the vials 2 (see FIG. 2c). The apertures 22 are arranged in a regular two-dimensional array, in the illustrated embodiment in a matrix array consisting of rows and columns extending perpendicularly thereto, which are offset from one another at equal distances and which are offset relative to each other in a periodic arrangement.

The apertures 22 are surrounded by cylindrical side walls 37 (see FIG. 2b) on the upper side of the carrier 20, which are preferably formed as circumferential side walls, but may also be formed as relatively short side wall portions for delimiting an associated aperture 22 only partially. In each case, a collision of containers, which are accommodated in directly adjacent apertures 22, is prevented by the side walls 37.

FIG. 2c shows a greatly enlarged detail from FIG. 2b. Four elastic supporting tongues 23 each protrude into the apertures 22, which are disposed along the edge of the apertures under equal angular distances from one another and which are separated from each other via a slot 24. The supporting tongues 23 are in particular formed integrally with the plate 21 of the carrier 20, which can be implemented easily using a conventional 1-component injection molding process or a 2-component injection molding process. Upon insertion of a container, the supporting tongues 23 are first pivoted elastically in order to snuggle to the constricted neck portion 5 of the container 2 after elastically pivoting back (see FIG. 3c) or to support the containers in this area, as described below. Because the resilient supporting tongues 23 project into the apertures 22 in an arrangement with a point symmetry of higher order, this results in a symmetrical force distribution when supporting the containers by the supporting tongues 23, so that the containers are automatically centered with respect to a center line of a respective aperture 22.

As can be seen in FIG. 2c, a plurality of protrusions 40 protrude from the upright, circumferential side wall 35 of the carrier 20, which are interrupted in a predetermined geometry by slots 41, which is, however, not absolutely necessary.

FIGS. 2d and 2e show a supporting frame for supporting a carrier 20 to form a supporting structure according to a first embodiment of the present invention. According to FIG. 2e the frame 50 is formed by a circumferential side wall 51 which merges into a flange-shaped circumferential upper rim 53. The frame is open on the upper side and bottom side so that the side wall 51 surrounds an aperture 55. According to FIG. 2e a plurality of ribs 52 are formed on the inner side of the side wall 51, which may serve, on the one hand, for stiffening of the frame 50 and which, on the other hand, may serve for a unique definition of the position of a carrier 20 due to their geometrical arrangement in a such a framework 50, as described above.

As shown in FIG. 2e, the ribs 52 do not necessarily have to extend over the entire height of the side walls 51 so that they together form a plurality of support points for supporting the carrier. According to FIG. 2e, a protrusion 54 is formed at the lower edge of the side wall 51 that is formed in this example circumferential (which is not essential) and which projects inward into the aperture 55.

According to the invention the frame 50 and the carrier 20 are adapted to one another in such a manner that the carrier 20 can be accommodated in the frame 50 and that the protrusions 40 on the side wall 35 of the carrier (cf. FIG. 2c) rest directly on the supporting points on the upper ends of the ribs 52 in a first orientation of the carrier (first carrier orientation). In contrast, when the carrier 20 is turned over and is inserted into the frame 50 in a second orientation (i.e. in the opposite orientation or second carrier orientation), the ribs 52 on the sidewall 51 of the frame 50 are in engagement with the slots 41 between the protrusions of the carrier 20, so that the carrier 20 can slide down along the side wall 51, until finally the protrusions 40 rest on the bottom rim 54 of the frame 20.

According to the invention the supporting tongues 23 are configured for supporting the containers on the carrier 20 in both orientations of the carrier 20 (i.e. in the two orientations of the containers, namely upright or upside down) so that they are retained in axial direction. This is illustrated by way of example in the comparative view in FIGS. 3h and 3i. According to FIG. 3h the containers are inserted into the apertures of the plate 21 of the carrier 20 upside down, i.e. with their expanded upper rim 6 facing downwards (first orientation), such that the upper rim extends beyond the plate 21 and that the containers are supported on the supporting tongues of the plate 21 in the region of the constricted neck portion, as described above with reference to FIG. 2c. The carrier 20 is inserted from above into the supporting frame 53 (i.e. in the first carrier orientation) such that the protrusions 40 on the side wall of the carrier 20 (see FIG. 2c) rest on the protrusion 54 on the lower rim of the side wall 51 of the frame 50 (see FIG. 2e). As is indicated by the dashed line in FIG. 3h, in this position the lower ends of the containers 2 (i.e., in FIG. 3h the filling apertures of the carpoules or cartridges 2) are arranged under a predetermined distance (a first distance) from the upper surface of the upper rim 53 of the supporting frame 50.

In the opposite orientation according to FIG. 3i, i.e. when the carrier 20 is turned over, the carrier 20 is inserted from above into the supporting frame 53 (i.e. in the second carrier orientation) such that the protrusions 40 on the side wall of the carrier 20 (see FIG. 2c) rest on the protrusion 54 at the lower rim of the side wall 51 of the frame 50 (see FIG. 2e). In this orientation, the cartridges 2 are suspended in the plate 21 of the carrier 20 (i.e. in the second orientation). I.e., the cartridges 2 are suspended in the plate 21 of the carrier 20 with their wider aperture at the upper rim 6, which is used for filling and subsequent inserting a stopper, directed upward and with their outlet aperture 8 directed downward. As indicated by the dashed line in FIG. 3i, in this position of the containers 2 the upper rims of the containers 2 (in FIG. 3i the wider apertures at the upper rim 6 of the cartridges 2) are arranged at the same predetermined distance (a second distance, which is equal to the above first distance) to the upper surface of the upper rim 53 of the supporting frame 50.

The same applies to the distance between the upper ends 6 of the cartridges 2 and the upper surface of the upper rim 53 of the supporting frame 50 as shown in FIG. 3h and for the distance between the lower ends of the cartridges 2 and the upper surface of the upper rim 53 of the supporting frame 50 as shown in FIG. 3i.

Thus, the supporting structure formed jointly by the carrier 20 and the frame 50 is matched to the lengths of the containers 2 in such a manner that in the position shown in FIG. 3i the upper ends 6 of the containers 2 are disposed at the same distance to the upper surface of the upper rim 53 of the supporting frame 50 as the lower ends 8 of the containers 2 in the position shown in FIG. 3h.

As can be concluded from FIGS. 3h and 3i, in both orientations the two ends of the containers 2 are freely accessible for the treatment or processing of the containers 2, because in both positions the ends of the containers 2 project beyond the upper and lower rim, respectively, of the supporting structure formed by the carrier 20 and frame 50.

For the transport and packing of the afore-mentioned supporting structure together with the containers accommodated therein, a transport and packaging container 10 us used, which is shown schematically in FIGS. 9a and 9b. According to FIG. 9a the transport and packaging container 10 is essentially box-shaped or trough-shaped and comprises a bottom 11, a circumferential side wall 12 protruding perpendicularly from this bottom 11, a step 13 substantially projecting perpendicularly from this and an upper rim 15, which is formed as a flange. The corners 16 of the transport and packaging container 10 are conveniently rounded. The upper side wall 14 may be slanted relative to a vertical onto the bottom 11 by a small angle of slope in order to facilitate the inserting of the supporting structure formed by a planar carrier 20. Such a transport and packaging container 10 is preferably formed from a plastics material, particularly by plastic injection molding, and is preferably formed of a clear transparent plastic to enable an optical visual inspection of the carrier 20 accommodated in the transport and packaging container 10 and of the containers 2 supported by the carrier 20.

For reliable positioning the carrier 20 in the transport and packaging container 10, the carrier and the transport and packaging container 10 comprise positioning structures which cooperate with each other, in particular in a form-fitting (positive-fit) manner. As an example, positioning structures may be formed at an appropriate position, particularly on the step 13 or on supporting surfaces 18 of the transport and packaging container 10, which are formed as protrusions or recesses or depressions, which interact in a form-fitting manner with correspondingly configured recesses or depressions or protrusions of the carrier 20 for positioning the carrier 20 precisely in the transport and packaging container 10. For this purpose a plurality of pin-like protrusions (not shown) may be formed particularly on the step 13 of the transport and packaging container 10, which engage in corresponding centering apertures 27 formed in the carrier 20.

According to FIG. 9a, the step 13 of the transport container 10 is formed as a circumferential, planar supporting surface on which the carrier 20 rests directly. According to further embodiments also additional supporting surfaces 18 or supporting members may be formed on the side walls 12 of the transport and packaging container 10. In this way, the carrier 20 can be positioned precisely in the transport and packaging container 10 and the plurality of containers 2 can be placed in this way in a regular array and at precisely defined positions in a transport and packaging container 10 having standard dimensions. In particular it can be ensured in this way that all bottoms of the containers 2 are arranged in a common plane and in parallel with the bottom 11 or upper rim 15 of the transport and packaging container 10.

Although the bottom 11 of the transport container 10 is shown in FIG. 9a to be closed and formed integrally with the side wall 12, the lower end of the transport container 10 may also be formed open in the manner of the upper end, in particular with a flange-like bottom rim in the manner of the upper rim 15 so that the bottoms of the containers 2 are freely accessible from the underside of the transport and packaging container 10, e.g. for processing steps in a sterile tunnel or in a freeze-dryer, as explained in detail below.

As shown in FIG. 9a, in the regular arrangement of FIG. 9a the plurality of vials 2 are disposed in a plane and distributed at predetermined constant distances along two mutually orthogonal directions. Generally, also other regular arrangements are conceived. For example, mutually adjacent rows and columns of containers 2 may also be offset by a predetermined distance to each other, namely in a periodic configuration with a predetermined periodicity. Thus, automated processing systems can expect the containers 2 at precisely predetermined positions when they are transferred to a processing station, which significantly reduces the automation effort. As explained in more detail below, according to the invention the containers 2 can also be processed together within the carrier 20 or within the transport and packaging container 10, in particular in a sterile tunnel or in a freeze-dryer or freeze-drying cabinet.

For enabling that the carriers 20 can be inserted easily into and removed from the transport and packaging container 10, access apertures 29 are formed on two longitudinal sides of the carrier 20, which can be used by gripping arms or the like to grip the carrier 20. The access apertures 29 may be arranged offset to each another, if viewed in the longitudinal or transverse direction of the carrier, which further simplifies an unambiguous positioning of the carrier 20 in the transport and packaging container 10.

While in the embodiment of FIG. 9a the carrier 20, which serves as a supporting structure, is formed as described above with reference to FIG. 2c, according to FIG. 9b flaps 30 are used as supporting means, which are pivotally mounted on pins 31 on the carrier 20 and are preferably resiliently biased into the supporting position, as this is shown in the insert in the lower left-hand part of FIG. 9b. In this supporting position, the expanded upper rim 6 of the container 2 rests directly on the front ends of the flaps 30. A restoring force can act on the flaps 30 such that the containers optionally can be supported either suspended upright in the carrier, as shown in the insert in the lower left-hand part of FIG. 9b, or that they rest upside down on the rear sides of the flaps 30 (not shown) in the transition region between the cylindrical side wall of the containers and the constricted neck portion. In the embodiment of FIG. 9b such a restoring force can be effected by the shape and supporting of the pins 31, possibly also by an additional returning means, or, in the case of an integral design of the supporting tongues with the carrier 20 of FIG. 9a. e.g. by the material and geometry of the supporting tongues.

The accommodation of a supporting structure, which is formed in two parts and formed by a supporting frame 50 and a carrier 20 according to FIGS. 2a to 2g, in a transport and packaging container 10, as described above, is shown in FIGS. 3a to 3g. The supporting structure can be supported directly on the bottom 11 of the transport and packaging container 10 or may be supported on supporting surfaces of the transport and packaging container 10. For example, the upper rim 53 of the supporting frame 50 may be supported on the upper ends of protrusions provided on the side wall 12 or on the bottom 11 of the transport and packaging container 10. In this way, according to the invention also more than two height levels of the ends of the containers 2 supported on the carrier 20 can be implemented.

Figure 3A:
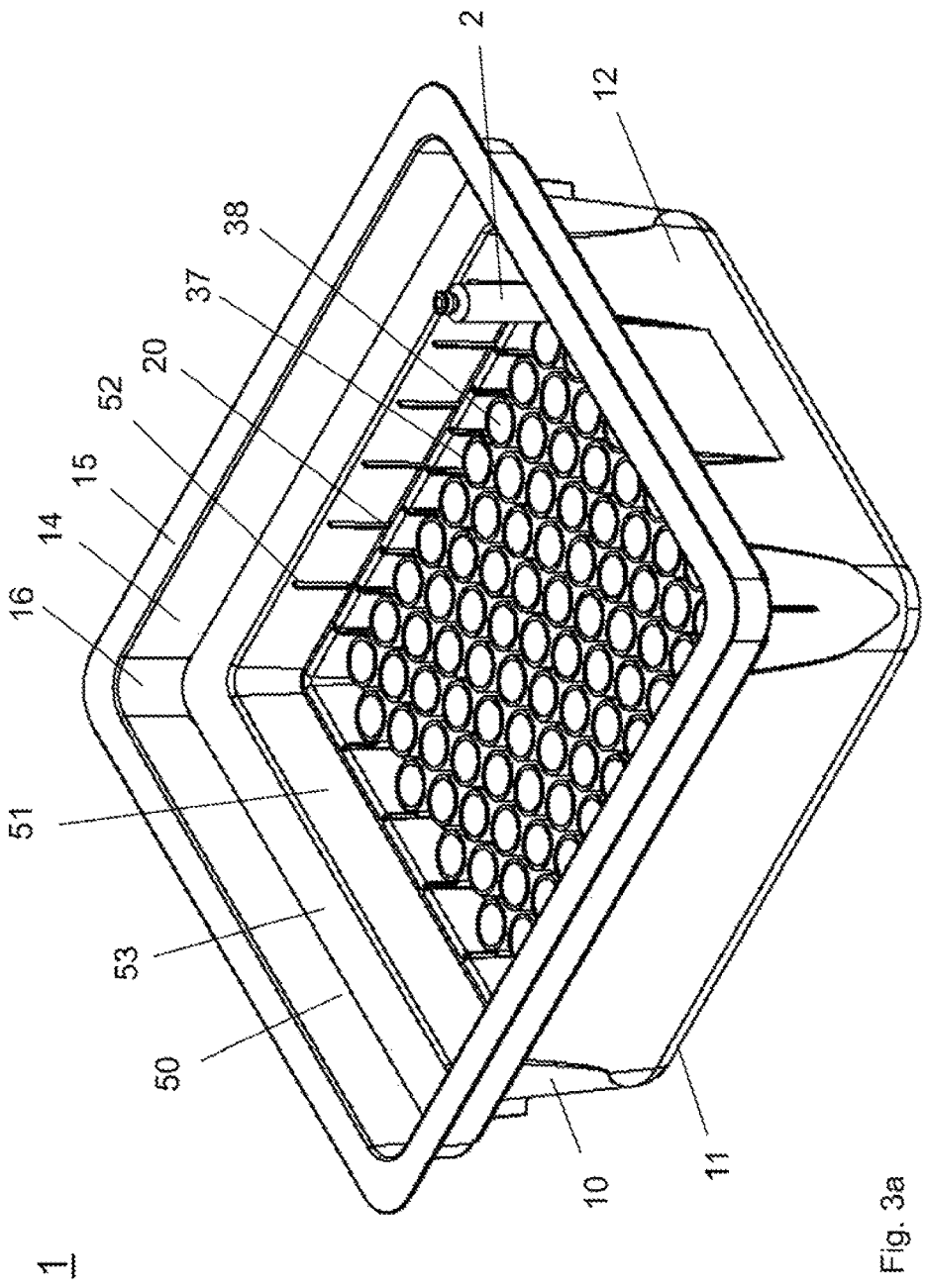
Figure 3C:
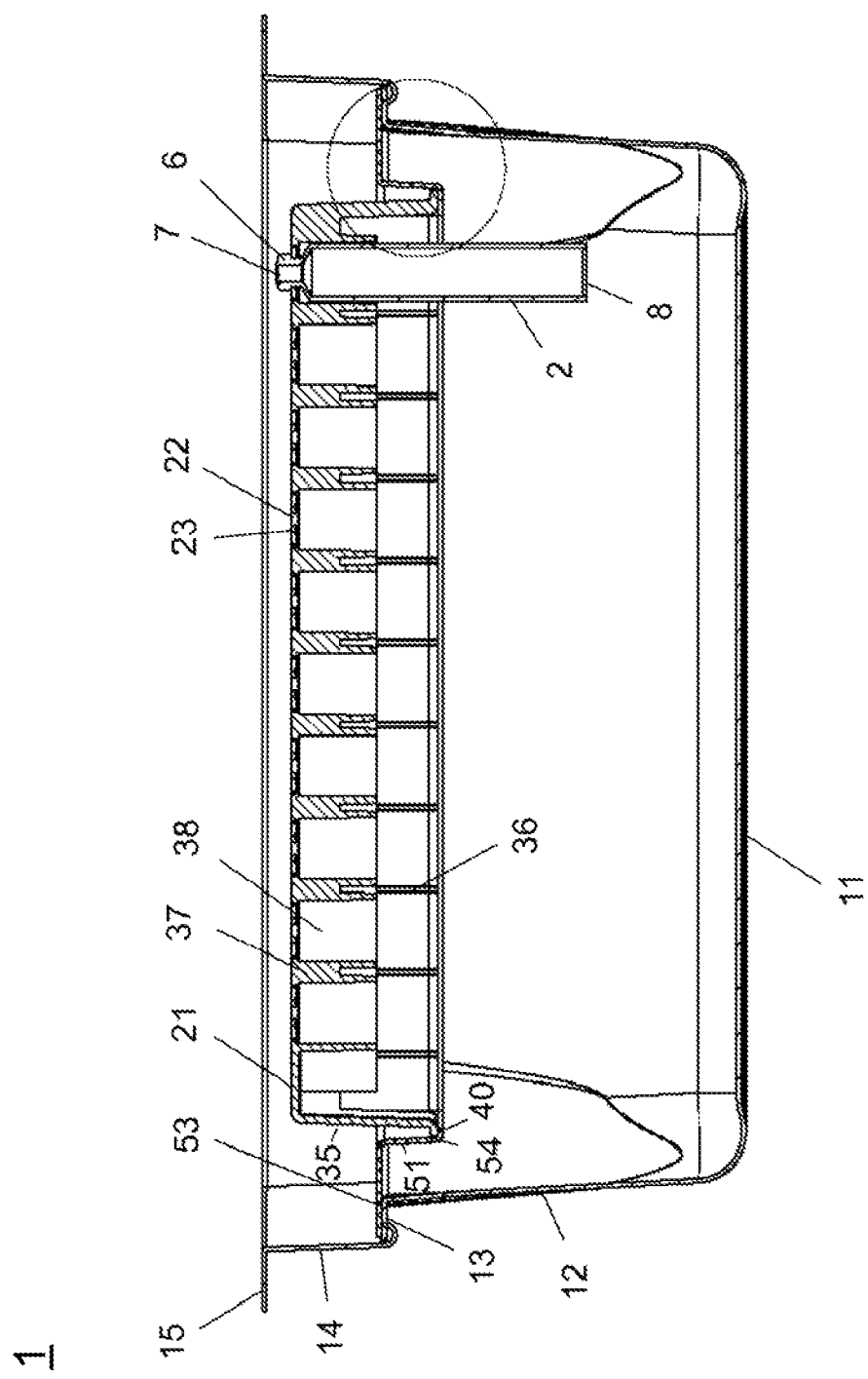
Figure 3D:
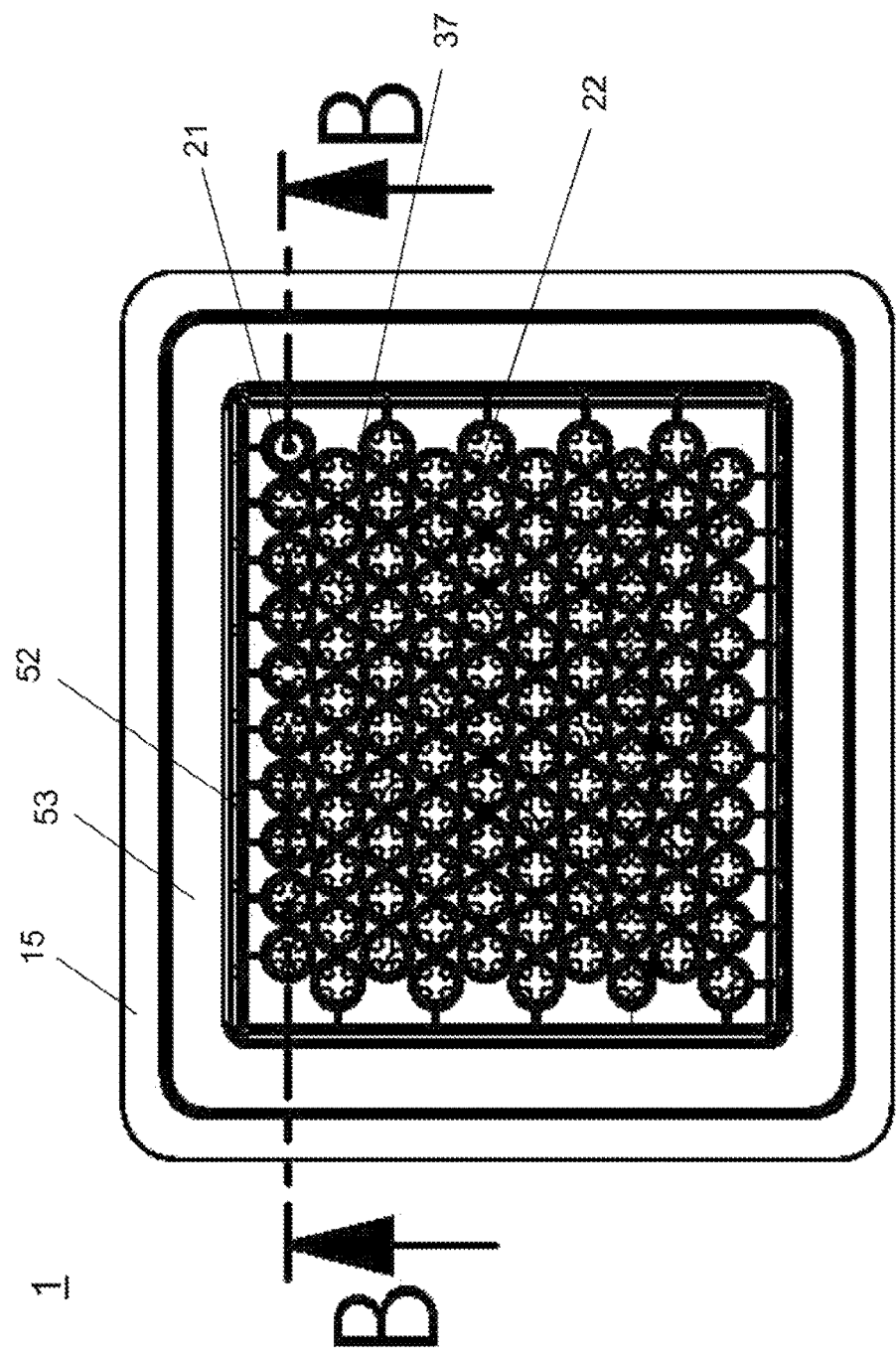
Figure 3E:
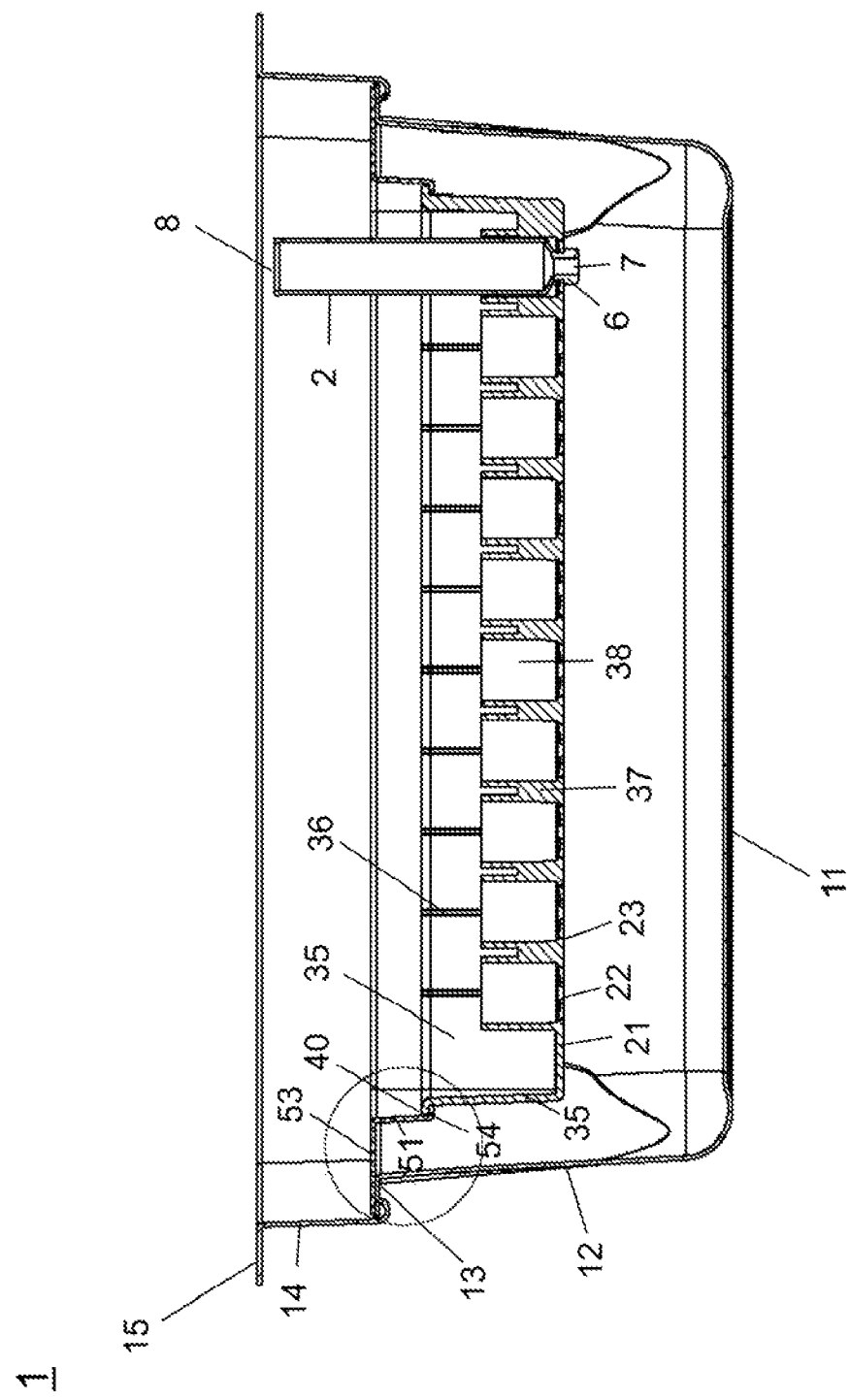
Figure 3G:
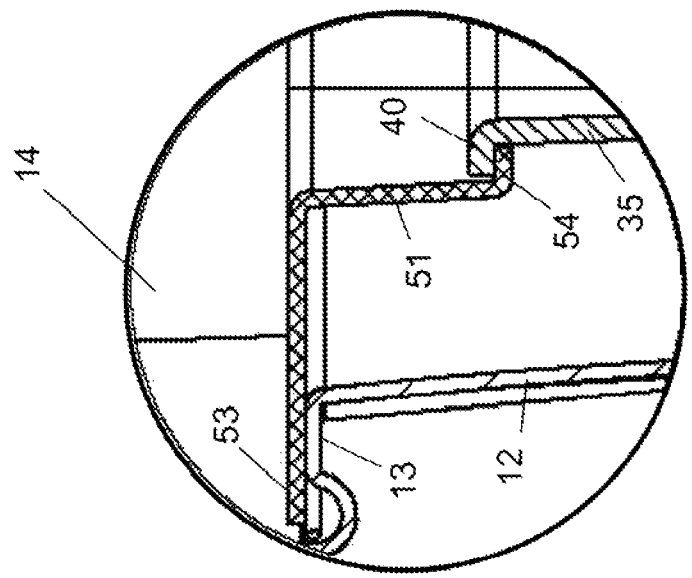
Figure 3F:
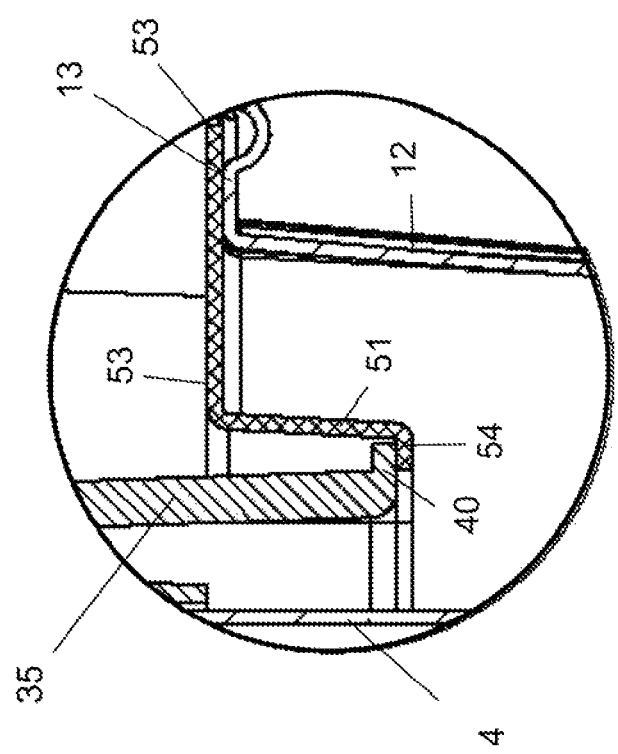

FIG. 3f shows the partial view encircled in FIG. 3c in a greatly enlarged view, namely in a position in which the carrier 20 is inserted into the frame 50 such that the cartridges 2 are suspended upright in the apertures 22 of the plate 21 of the carrier 20. In contrast, FIG. 3g, shows the partial view encircled in FIG. 3e in a greatly enlarged representation, namely in a position in which the carrier 20 is inserted into the frame 50 such that the cartridges 2 are inserted upside down into the apertures 22 of the plate 21 of the carrier 20 and that the cartridges 2 are arranged on the upper side of the carrier 20.

Figure 4G:
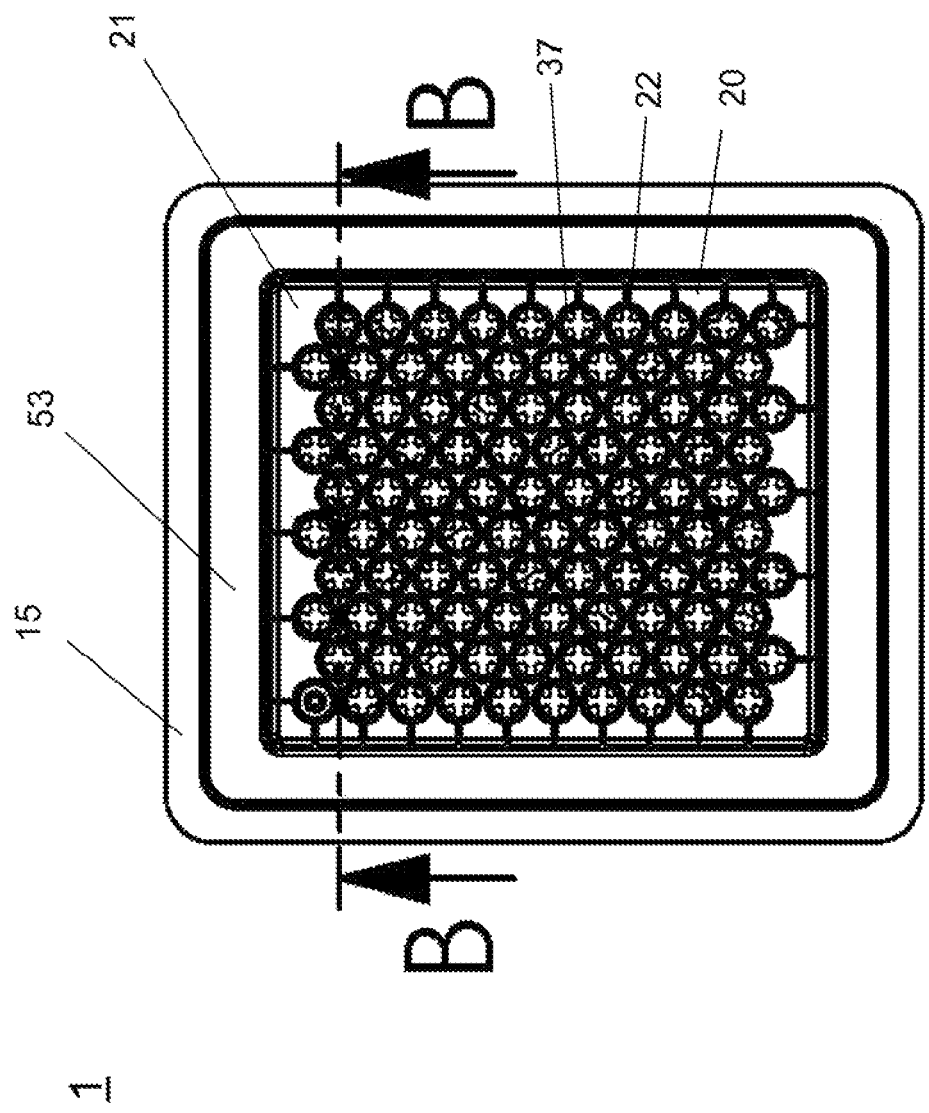

FIGS. 4a to 4j show the accommodation of a supporting structure according to a further embodiment of a transport and packaging container 10, as described above. As shown in FIGS. 4c, 4d and 4f, the front ends of containers, which are designed as cartridges, can be inserted into the apertures of the plate 21 of the carrier 20 in a first orientation such that the expanded upper rims slightly projects beyond the plate 21 and that the supporting tongues 2 respectively support or hold the cartridges 2 in the region of the constricted neck portions. Here, the front ends of the cartridges extend through the receptacles formed by the cylindrical side walls 37. The side walls 37 are provided with slots 37a and hence can be expanded slightly, e.g. for guiding and clamping the front ends of the cartridges. The side walls 37 thereby prevent a collision between cartridges supported directly adjacent to each other on the carrier 20.

Figure 4H:
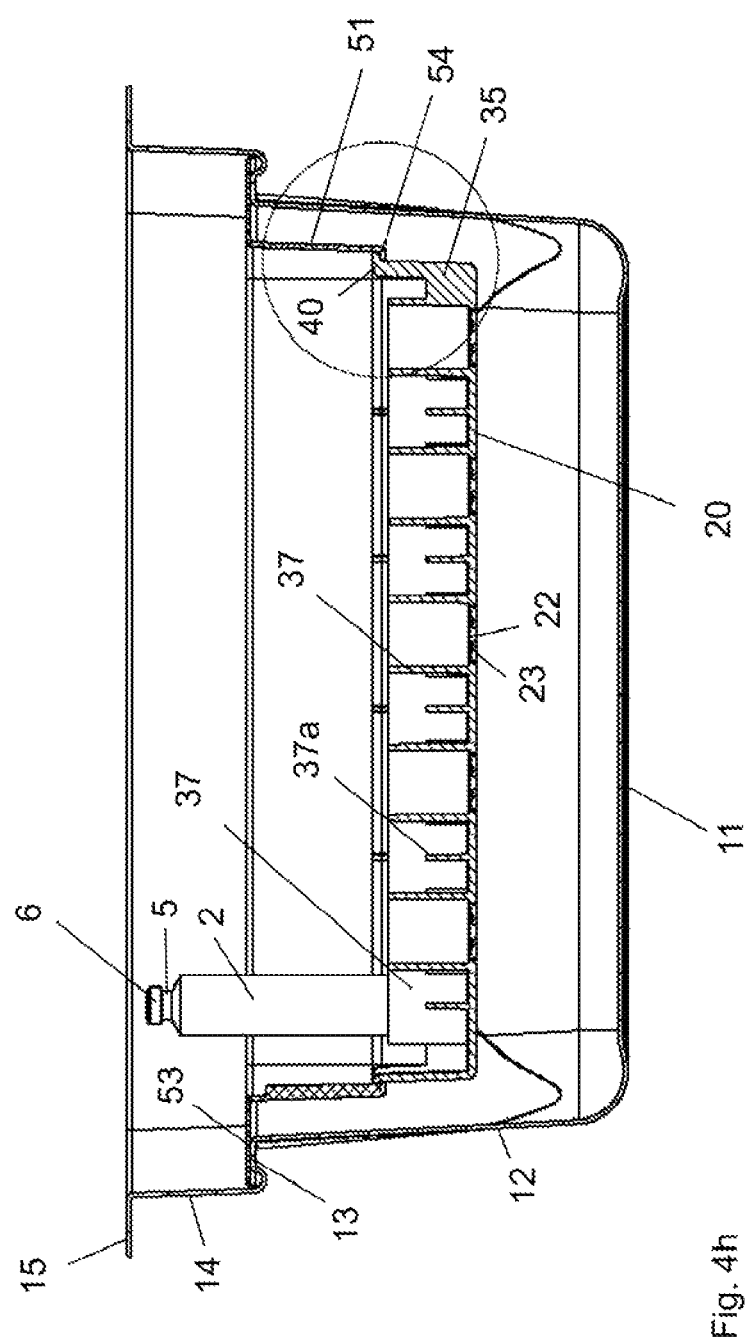
Figure 4J:
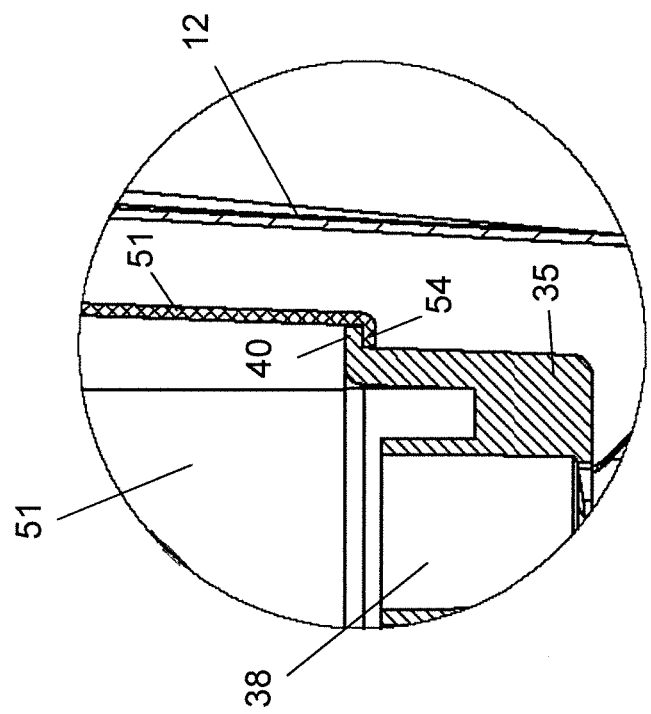
Figure 4I:
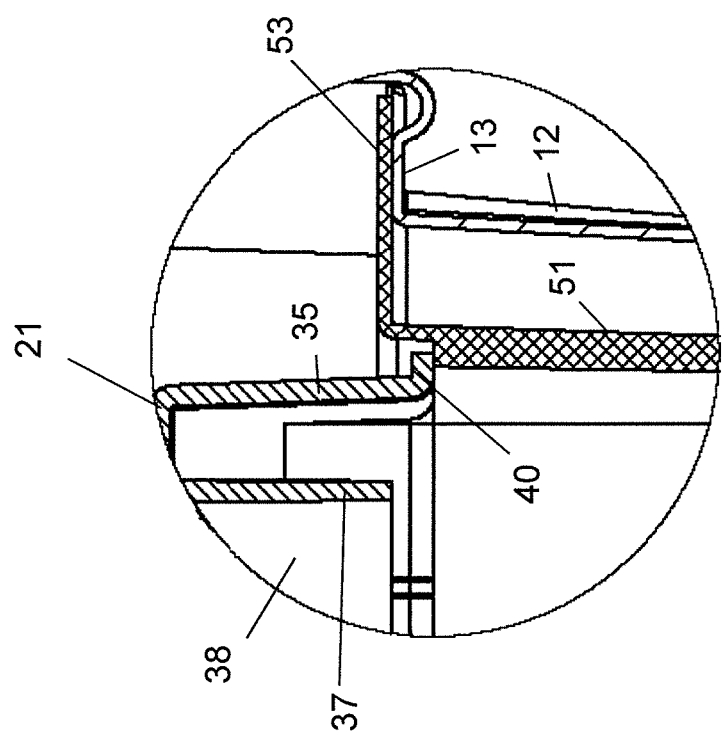
Figure 41:
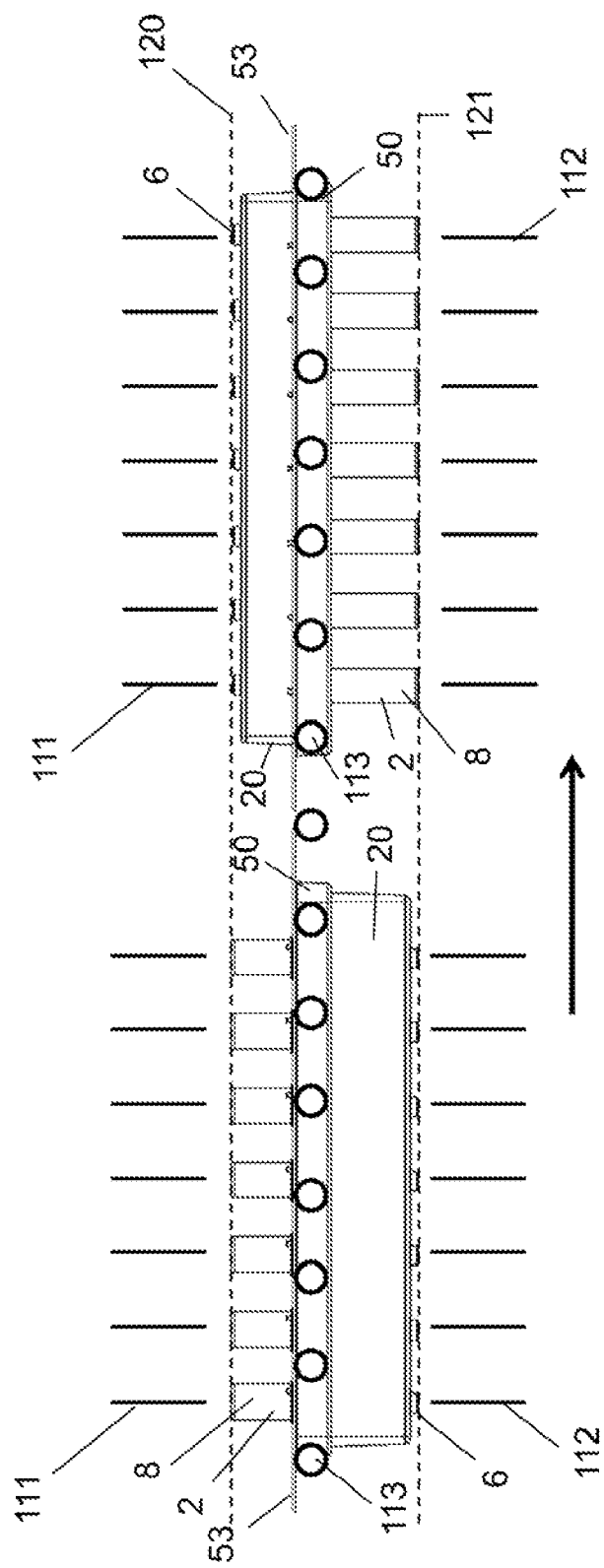

FIG. 4i shows the partial view encircled in FIG. 4f in a greatly enlarged view, namely in a position in which the carrier 20 is inserted into the frame 50 in a first carrier orientation such that the cartridges 2 are suspended upright in the apertures 22 of the plate 21 of the carrier 20. In the second position shown in FIG. 4f, the lower ends of the cartridges 2 are inserted into the receptacles formed by the side walls 37, so that they rest directly on the plate 21 of the carrier 20. Here, the side walls 37 can also clamp the lower ends of the cartridges 2 slightly.

FIG. 4j shows the partial view encircled in FIG. 4h in a greatly enlarged view, namely in a position in which the carrier 20 is inserted into the frame 50 in a second carrier orientation such that the lower ends of the cartridges 2 are inserted into the receptacles formed by the side walls 37 and that the upper ends of the cartridges 2 with the expanded upper rims 6 provided there are also directed toward the upper aperture of the transport and packaging container 10. Because in this position the front ends of the cartridges 2 are not inserted into the apertures of the plate 21 of the carrier 20, in the position shown in FIG. 4h the distance of the upper rims 6 of the cartridges 2 to the plate 21 of the carrier 20 is slightly larger than the distance of the lower edges 8 of the cartridges 2 to the plate 21 of the carrier 20 in the position according to FIG. 4f. This height difference substantially corresponds to the axial length of the constricted neck portion at the upper rim of the cartridges 2, and thus in the sense of the present application is negligible in comparison to the total length of the cartridges 2.

FIG. 4k shows the transport and packaging container described above in an exploded perspective view.

FIG. 4l shows a schematic diagram of a process for the concurrent treatment or processing of a plurality of containers according to the present invention. Here, a respective supporting structure is shown in the left-hand and right-hand part of the drawing, wherein in the left-hand part of the drawing the containers 2 are supported on the carrier 20 in the opposite orientation as in the right-hand part of the drawing. The supporting structures are conveyed by a conveying device 113, e.g. by means of conveying rollers or conveyor chains, in the direction of the arrow, i.e. in FIG. 4l from left to right. The conveying device 113 may act, for example on the upper rim 53 of the supporting frame 50. For reasons of simplicity, in FIG. 4l the associated transport and packaging container is not shown. However, as will be apparent to the person skilled in the art upon reading the above description the treatment or processing of the containers can be performed optionally either without such a transport and packaging container or while the supporting structure is accommodated in the transport and packaging container. If the bottom of the transport and packaging container is then designed to be closed, as shown for example in FIG. 9a, the treatment or processing of the containers may take place only from the upper insertion aperture of the transport and packaging container.

According to FIG. 4l, for the treatment or processing the containers supported on the supporting structure 2 are passed automated along processing stations 111, 112, which can be disposed above and/or below the conveying device 113. As can be seen in FIG. 4l, for the treatment or processing of the containers 2 there is no need to adjust the heights of the processing stations 111, 112 regardless of whether the containers 2 are supported on the supporting structure in the first position (namely, for example upright) or in the second position (namely, for example upside down), because, apart from the unavoidable tolerances as mentioned above, the upper and lower ends of the containers 2 are on the same height level in both positions (orientations). According to the invention this facilitates the treatment and processing of the containers considerably, because the effort regarding adjustment, control, and automation of the processing stations 111, 112 and of the conveying device 113 can be simplified substantially.

FIG. 5a shows a further embodiment of a supporting structure according to the present invention, wherein the supporting tongues 23 are formed as resilient supporting tongues which project arcuately from the upper side of the plate 21 of the carrier and which extend radially inward into the associated apertures of the plate 21 of the carrier. In particular it can be seen that in the home position or supporting position, the cartridges are preferably supported in such a manner that a radial clearance is provided between the front ends of the supporting tongues 23 and the constricted neck portions 5 of the cartridges and that therefore the bottoms of the expanded upper rims 6 of the cartridges rest on the front ends of the supporting tongues 23 in the position shown in the left-hand part of FIG. 5a, or that the transition regions between the constricted neck portions 5 and the cylindrical side walls 4 of the cartridges rest loosely on the rear sides of elastic supporting tongues 23 in the position shown in the right-hand part of FIG. 5a. In this way, in both orientations the cartridges can be retained to the plate 21 in one axial direction. The dashed line in FIG. 5a indicates the same height level of the upper rims 6 of the cartridges and of the lower ends 8 of the cartridges when these are supported on the plate 21.

FIG. 5b shows in a partial sectional view the supporting tongue of a supporting structure according to a further embodiment. As can be seen, the resilient supporting tongues 23 are flag-shaped and are formed with a supporting nose projecting radially inward. According to FIG. 5b, the resilient supporting tongues 23 are connected with the plate 21 via a resilient base 23a projecting perpendicularly from the upper side of the supporting plate 21. The base 23a merges into a portion 23b curved radially inward, which finally passes into the supporting nose 23c on which the expanded upper rim 6 of the container (see FIG. 1) rests. The supporting nose 23c protrudes into the aperture of the plate 21 of the carrier. The supporting nose 23c is followed by an insertion slope 23f extending obliquely upward, which connects with the upper end of the supporting tongue 23. A recess 23d is formed between the upper insertion slope 23f and the lower insertion slope 23b, in which the upper rim 6 is retained in both axial directions (that is suitable for an upright orientation or for an upside-down orientation) and accommodated with a radial clearance. Due to the insertion slope 23f on the upper side of the supporting tongue 23 and the curved portion 23b of the supporting tongue 23, which is open downward, the containers may be inserted into the apertures of the plate 21 of the carrier optionally either from above or from below and withdrawn again.

Upon insertion of the containers from above into the apertures of the carrier first the bottoms or lower ends of the containers get in abutment with the insertion slopes 23f of the supporting tongues 23. When the containers are further inserted, the lower ends or bottoms of the containers slide down along the insertion slopes 23f and resiliently spread the supporting tongues 23 progressively apart or fold and swivel them back. When the containers are further inserted, finally the cylindrical side walls 4 of the containers get in contact with the supporting noses 23e and slide therealong, until eventually the undersides of the expanded rims 6 of the containers rest loosely on the supporting noses 23c of the supporting tongues 23. The containers can be removed from the apertures of the plate 21 of the carrier either upward with the opposite movement of the supporting tongues 23 or downward with resilient bending of the supporting tongues 23.

Upon insertion of the containers from below into the apertures of the carrier, first the upper ends of the containers get in abutment with the curved portions 23b of the supporting tongues 23. Upon further introduction of the containers, the upper ends of the containers slide along the curved portions 23b upward and resiliently spread the supporting tongues 23 progressively apart or fold or swivel them back until finally the supporting noses 23c are reached. When further pushing up the containers, the bottoms of the expanded rims 6 of the containers slide over the supporting noses 23c of the supporting tongues 23 and finally rest loosely on the supporting noses 23c of the supporting tongues 23. The containers can be removed from the apertures of the plate 21 of the carrier either downward with the opposite movement of the supporting tongues 23 or upward with resilient bending of the supporting tongues 23.

In the embodiment of FIG. 5b thus the expanded upper rim portions 6 (rolled edge) of the containers are embraced clamp-like and in a positive-fit manner, while a sufficient radial clearance, as described above, is ensured, as indicated in FIG. 5b by the air gap in the radial direction. Furthermore, a sufficient axial clearance can also be ensured, as indicated in FIG. 5b by the air gap in the axial direction.

Figure 6C:
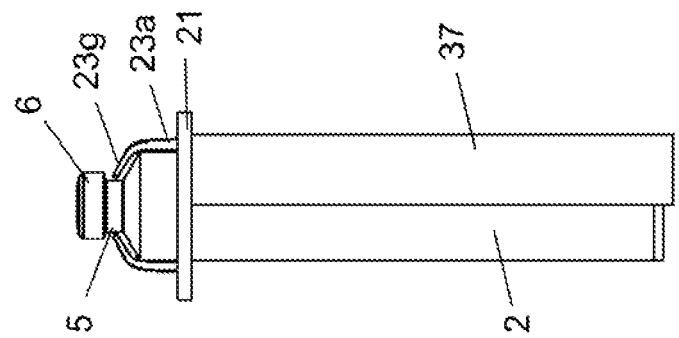
Figure 6B:
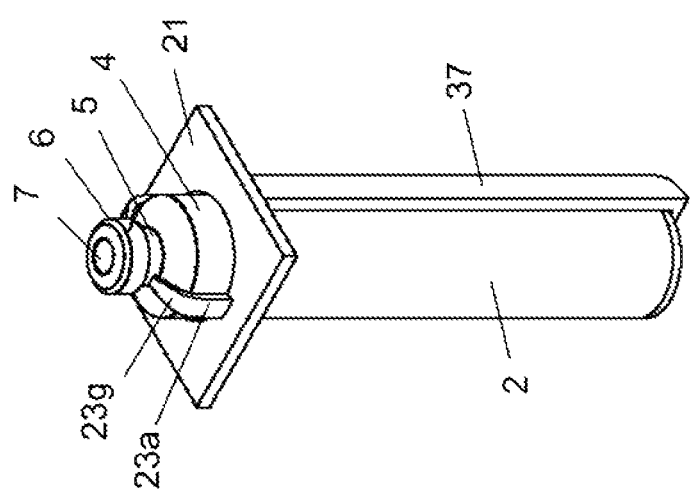
Figure 6A:
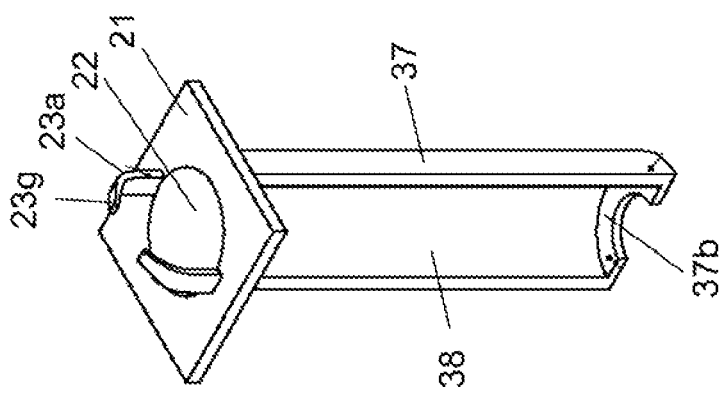

FIGS. 6a to 6h show further variants for supporting the containers on a carrier, which can be provided additionally or alternatively to the supporting described above. FIG. 6a shows a side wall formed as a half-shell 37, which projects from the underside of the plate 21 of the carrier and comprises a protrusion 37b projecting at its lower end radially inward, in which a recess is formed. This protrusion 37b can be used as a stop for defining the axial position of the container 2 on the carrier, as shown in FIG. 6b, where the bottom of the expanded upper rim 6 of the container 2 rests loosely and preferably with radial clearance on the front ends 23g of the supporting tongues 23a. FIG. 6c shows a side view of the carrier of FIG. 6b. As can be seen in FIG. 6c, due to the design of the side wall 37 as a half-shell, the entire left-hand half of the container 2 is freely accessible from the side of the supporting structure, for example for processing, handling or for an (optical) inspection of the container or of its content. Because only two supporting tongues 23a are respectively associated to the apertures of the carrier (on mutually diametrically opposite sides of the apertures), also the entire upper end of the container 2, including the constricted neck portion 5, is freely accessible from the side of the carrier, for example for a processing, handling or for an (optical) inspection of the container or of its content, as described below with reference to FIG. 6i. FIGS. 6d and 6e show additional side views of this supporting structure.

Finally FIG. 6f shows a further embodiment in which the side wall 37 is shorter than the side wall of the container 2 and thus the entire lower end of the container 2 is freely accessible from the underside of the carrier. In the case of the embodiment of FIG. 6a, however, if a cartridge is used, the lower edge of the cartridge is supported on the protrusion 37b, but the filling aperture of the cartridge at the lower end of the cartridge is freely accessible, for example for filling the cartridge (carpule).

FIGS. 6g and 6h show this supporting structure in a plan view and in a bottom view.

FIG. 6i shows as an example the measurement of the filling level or of the filling capacity of a container formed as a cartridge by means of a laser 100. It is assumed that the cartridge is filled via the filling aperture at the upper rim 6 by means of an injection needle 110. The hatched area 9a indicates the already-filled portion of the cartridge, whereas above this area an unfilled area 9b exists, which is, for example, filled with air or an inert gas. The laser beam 101 of the laser 100 propagates through the constricted neck portion 5 of the cartridge. The laser beam 101 is detected on the opposite side of the cartridge by means of an optical sensor 102. When the cartridge is also filled in the area of the laser beam 101, a lateral displacement or deflection of the laser beam 101 occurs due to the different optical conditions along the beam path, which can be detected with the sensor 102. Because the laser beam 101 may be collimated to a relatively small beam diameter, in this manner also the current filling capacity of the cartridge can be detected precisely and a treatment or processing of the cartridge such as a filling operation can be stopped, for example, upon reaching a predetermined filling level.

FIGS. 7a to 7f show a supporting structure according to a further embodiment of the present invention. Instead of the supporting tongues described above, in this embodiment cylindrical or hollow cylindrical pins 42 protrude from the plate 20 of the carrier substantially perpendicularly for preventing contact of containers supported directly adjacent to each other on the carrier 20.

In the plan view of FIG. 7b and in the greatly enlarged partial view of FIG. 7c it can be seen that the carrier 20 is substantially open and is spanned by intersecting supporting webs 43 which form a mesh-like bottom of the carrier on which the pins 42 are arranged. According to FIG. 7c six support pins 42 respectively form a receptacle in which the lower end or the upper end of the container is accommodated. Here, a radial clearance can be present between the supporting pin 42 and the side wall 4 of the container. Or the supporting pins 42 may abut tangentially to the side wall 4 of the container and possibly even clamp it slightly. Here, the intersecting support webs 43 support the respective ends of the containers.

As can be seen in FIG. 7d and the greatly enlarged partial view of FIG. 7e, the containers 2 (in the drawings shown as cartridges) can be inserted upright or upside down into the receptacles formed by the pins 42. According to FIG. 7d such a carrier is accommodated directly in the transport and packaging container 10.

Of course, according to a further embodiment also an additional supporting frame can be provided, in which the carrier is in turn accommodated, as described above with reference to FIGS. 2. FIG. 7f shows a transport and packaging container 10 according to such a further embodiment in a perspective exploded view.

According to FIG. 7c, a recessed portion may be formed in the region of the crossing point 44 of the intersecting supporting webs 43 to form a receptacle for a constricted neck portion 5 of the container (see FIG. 1) to be supported, for preventing a tilting of the containers supported on the carrier. This results in a slight difference between the distance to the carrier 2 at which the upper ends 6 of the containers 2 are arranged in the first position, and the distance to the carrier 2 at which the lower ends 3, 8 of the containers 2 are arranged in the second position. However, this substantially corresponds to the axial length of the constricted neck portion 5 of the container to be supported, and is thus usually negligible compared with the total length of the containers.

In the plan view of FIG. 7b and in the greatly enlarged partial view of FIG. 7c it can be seen that the carrier 20 is formed substantially open and is spanned by intersecting supporting webs 43 which form a mesh-like bottom of the carrier on which the pins 42 are arranged. According to FIG. 7c six support pins 42 respectively form a receptacle in which the lower end or the upper end of the container is accommodated. Here, a radial clearance can be present between the supporting pin 42 and the side wall 4 of the container. Or the supporting pins 42 may abut tangentially on the side wall 4 of the containers and possibly even clamp them slightly. Here, the intersecting supporting webs 43 support the respective ends of the containers.

FIG. 8a shows a supporting structure according to a further embodiment of the present invention in a plan view. Like in the embodiment of FIG. 7a, according to FIG. 8a cylindrical or hollow-cylindrical pins 42 project substantially perpendicularly from the bottom 21 of the carrier 20 for preventing a collision of directly adjacent containers supported on the carrier 20. The pins are connected with each other via webs 47 which serve for stiffening the bottom 21. Overall, six pins 42 are respectively arranged around the respective apertures 22 of the carrier 20 under equidistant angular distances to form a receptacle, in which a container is to be accommodated. Besides the apertures 22, the bottom 21 of the carrier 20 is closed and is preferably formed from a plastic material. An elastic material, such as rubber or a soft, resilient plastic, can be applied around the apertures 22 to form a ring-shaped structure serving as a sealing member, as described in the following with reference to FIGS. 8c-8e. Particularly two-component injection molding techniques are suited for this purpose. Such a sealing member can also be positioned as a separate sealing gasket around the apertures 22 on the bottom 21 of carrier 20.

According to FIG. 8a the carrier 20 is trough-shaped, with a relatively wide rim 40, which is connected with the bottom 21 via side walls that are slightly inclined inward. Ribs 46 are formed on the inner sides of the side walls 35, which serve as spacers when a plurality of such carriers 20 is stapled in a stack one above the other.

FIG. 8b shows the portion encircled in FIG. 8a in a greatly enlarged view.

With reference to FIGS. 8c-8e, in the following a process according to the present invention will be described, which is used to close the rear end of a cartridge (cylinder ampoule) with a rubber stopper. It is expressly noted that this process can be performed also outside of a carrier, as described above, and that this process represents an independent invention, which can be explicitly claimed by the present application independently to the above embodiments.

The filling and sealing of pre-sterilized cartridges is of particular interest because it must be ensured that the drug stored in the cartridge retains its properties for years. To prevent an interaction of the drug with air, according to the invention the cartridge is evacuated, and then a stopper is inserted into the rear end of the cartridge to close it.

According to FIG. 8c the stopper 80 is inserted by a vacuum gripper 70 in a compressed state inside a cylinder 71 and held compressed in the cylinder 71. The outer diameter of the cylinder 71 is smaller than the inner diameter of the cartridge 2. Furthermore, the inner diameter of the cylinder 71 is smaller than the outer diameter of the stopper 80 when it is not compressed. The vacuum gripper 70 can be displaced in axial direction together with the cylinder 71, but can be displaced in axial direction relative to the cylinder 71.

A liquid 9a is filled into the cartridge 2, of which only the rear end is shown in FIGS. 8c to 8e. Above the liquid level 9c of the liquid 9a, the inner volume 9b of cartridge 2 is not filled. According to FIG. 8c an annular sealing member 77 is fitted onto the rear end of the cartridge 2, which is here flat (i.e. without a finger handle), to seal the rear end of the cartridge 2 against the environment. The cylinder 71 can be inserted by the vacuum gripper 70 into the aperture of the sealing member 77, because the outer diameter of the cylinder 71 is smaller than the diameter of the aperture.

At the front end of the cylinder 71 there is a plunger 73, which is sealed against the cylinder 71 by a sealing ring 74. The cylinder 71 and vacuum gripper 70 can be displaced relative to the plunger 73 in axial direction. The plunger 73 serves as an abutment surface which abuts against the sealing member 77 and can exert a pressure on the latter. According to FIG. 8c a radial suction channel 75 is formed inside of the plunger 77, through which the air or gas can so be evacuated out of the annular gap 76 between the cylinder 71 and the cartridge 2 by a suction device (not shown). The sealing member 77 may consist of an elastic rubber material and can be positioned on the rear edge of the cartridge 2. However, the sealing element can also be the bottom 21 of a carrier 20 (see FIG. 8) or the sealing member can also be disposed or applied around the respective aperture 22 in the bottom 21 of the carrier 20. When the cartridges rest upright on the bottom 21 of a carrier 20, which is closed as shown in FIG. 8a, the sealing arrangement shown in FIG. 8c can be implemented automatically when the cartridges 2 are inserted upright into a carrier. This position can in particular also be the transport position, in which the cartridges 2 are inserted into a carrier (nest) and in which the carrier is stored under sterile conditions and transported in a transport and packaging container such as shown, for example, in FIG. 7d.

The closing or sealing process starts with the setting of the stoppers: a sorting bowl (not shown) conveys stoppers 80 to the vacuum gripper 70 which is used to push then onto the cartridge afterwards. The vacuum gripper 70 pushes the stopper 80 into the cylinder 71 and the stopper 80 is thereby compressed, as shown in FIG. 8c. Subsequently, the vacuum gripper 70 is placed on the rear edge of the cartridge 2 together with the cylinder 71 and the plunger 73, whereby the sealing element 77 is pinched between the plunger 73 and the rear edge of the cartridge 2 to seal the inner volume 9b, which is not filled with liquid, and the annular gap 76 between the cylinder 71 and the cartridge 2 against the environment.

Air is then sucked out of the inner volume 9b that is not filled with liquid through the suction channel 75. Subsequently, the vacuum gripper 70 is displaced in axial direction relative to the cylinder 71 toward the liquid surface 9c. Here, the stopper 80 is first pushed out of the cylinder 71, so that it relaxes and bears sealingly on the inner wall of cartridge 2. Subsequently, the vacuum gripper 70 is further displaced in axial direction relative to the cylinder 71 towards the liquid surface 9c until the stopper 80 rests on the liquid surface 9c, as shown in FIG. 8d. After separation of the vacuum gripper 70 and the stopper 80, the sealing arrangement can be released, and the vacuum-gripper 70 and the cylinder 71 can be displaced again in axial direction out of the rear end of the cartridge 2, as shown in FIG. 8d.

Subsequently, the vacuum gripper 70 is further displaced relative to the cylinder 71 in axial direction, as shown in FIG. 8e, and the vacuum gripper 70 together with the cylinder 71 is displaced in axial direction out of the rear end of the cartridge 2 so that a new closing or sealing process can start.

During this closing or sealing process an optical inspection can check whether the stoppers are actually present. Furthermore, the positions of the cartridge, of the stopper and/or of the vacuum gripper can be determined and suitably adjusted. In a further part of the closing or sealing process a towing train can put caps onto the stoppered cartridges. These caps can be in particular metal lids that are crimped onto the rims of the cartridges. These caps can be conveyed by a sorting bowl.

A filling of containers, especially of cartridges, under vacuum, which can prevent the formation of bubbles, is usually carried out with rotary piston pumps. The art of handling viscous liquids under vacuum is to find a balance of the various parameters. With conventional methods a too strong vacuum can cause that the product starts boiling. In the conventional setting of stoppers in turn there is the risk that the product is extracted out of the cartridge past the stopper. However, if the vacuum is too low, air pockets or bubbles do not occur.

By means of the width of the annular gap 76 (see FIG. 8c) and of the suction channel 75 and the vacuum used for suctioning, according to the present invention appropriate parameters can be determined easily, so that stoppers can be set without boiling of the liquid but also without air pockets or bubbles in the liquid. It is a positive side-effect that by means of the afore-mentioned closing or sealing process a higher sterile safety level can be attained with only a small amount of air present in the cartridge, that the dosing accuracy is usually higher and that a potential displacement of the stopper caused by changing climatic conditions (air pressure) during transport can be eliminated.

In particular, the above-mentioned closing or sealing process can be also carried out such that the containers, in particular cartridges, are supplied to a sealing station in a carrier, as described above, and in a predetermined geometric arrangement, wherein the open ends of the containers are positioned as close as possible to the bottom of carrier. For example, the open end of a container can be supported directly on the bottom of the carrier or the open ends, for example the necks of the containers, may extend to the other side of the carrier through the apertures formed in the bottom of the carrier. Thus, the bottom of the carrier can act directly as a counter member for the plunger of the sealing station. The containers are supported on the carrier in such a manner that the open ends thereof are disposed in alignment with the apertures in the bottom of the carrier. Subsequently, the plunger of the sealing station approaches the open end of the container, as described above, and the sealing or closing operation is performed, as described above, while the containers are supported on the carrier.

FIG. 9c shows in a greatly enlarged partial view a further embodiment of a packing unit 1 comprising a supporting plate 21 of a carrier, as described above with reference to FIGS. 9a and 9b, which is accommodated in the transport and packaging container 10. According to FIG. 9c the transport unit 1 comprises measures for identifying and/or tracking as follows: as shown in the enlarged insert of FIG. 9c, an electronic RFID chip that can be read-out wirelessly or a RuBee chip 60 (a RuBee chip transmits at frequencies that can penetrate metal and water) is disposed in the region of the access aperture 29 (cf. FIG. 9a) between the supporting plate 21 and the side wall 12 and/or the step 13 of the container 10, which can be read out in a contact-less manner through the side walls of the packaging unit 1 and which outputs information with regard to identity, important product characteristics (manufacturer, content, production date, expiry date, . . . ) if queried. The chip 60 may be glued into the packaging unit 1 at a suitable position, also at a different position than shown in the drawing. The chip 60 may be disposed in such a manner that in the case that the packaging unit 1 is opened or that the supporting plate 23 is taken out of the packaging unit 1, the chip 60 is destroyed, for example is broken or getting inoperative. Due to lack of response from the chip 60 to a radio query, therefore information is available, which indicates that the packaging unit must have been manipulated in some way since the previous packaging process, because the chip 60 does not respond to the radio query. This can for example be used to prove the authenticity and integrity of the packaging unit and of the containers accommodated therein.

According to a further preferred embodiment, the RFID chip or RuBee-chip 60 is integrated in combination with other sensors that can monitor important parameters of the transport and packaging container 1 as a function of time that affect important quality or authenticity characteristics of the containers accommodated in the transport and packaging container 1. These quality or authenticity characteristics can be recorded and stored periodically in a memory associated with the chip 60 or sensor. For an electric power supply of these electronic components an independent power supply can be provided in the transport and packaging container 1, in particular a battery of small dimensions or also inductively by means of small circuit loop. In accordance with the present application in particular the following sensors are conceived:

- a moisture sensor with or without a memory (data logging) which periodically measures the humidity prevailing in the transport and packaging container and records it as required;
- a gas sensor with or without a memory (data logging), which measures the concentration of gases that are present in the transport and packaging container such as $O_2$, ozone or $CO_2$ or of sterilizing gases such as ethylene oxide, formaldehyde, and records as required;
- a temperature sensor with or without memory (data logging) which periodically measures the temperature in the transport and packaging container and records it as required;
- an UV sensor with or without a memory (data logging), which periodically measures UV radiation penetrating into the transport and packaging container and records it as required;
- a gamma ray sensor, electron beam sensor or X-ray sensor with or without storage (data logging), which periodically measures the radiation penetrating into the transport and packaging containers and records it as required.

As will become apparent to the person skilled in the art upon reading the foregoing description, the containers may be supported on the supporting structure also by means of any other positive or frictional coupling.

The supporting force exerted by the supporting means on the containers is sufficient to support the containers reliably on the supporting structure. In particular, the supporting force exerted is greater than the weight of the containers, if necessary together with the content and a sealing stopper. Thus, a reliable supporting of the containers on the supporting structure is ensured. At the same time the containers can be displaced in the apertures or receptacles of the supporting structure without any major effort, in particular displaced forward in axial direction or rotated.

Of course, in the sense of the present invention the supporting structure (the carrier) can also be formed of a thermoplastic, thermosetting or elastomeric plastic, wherein at least portions of the supporting structure or of the carrier are provided with a coating reducing friction, to facilitate insertion and removal of the containers.

As will become apparent to the person skilled in the art upon reading the foregoing description, the various aspects and features of the embodiments described above may be combined in any manner with one another, resulting in numerous further embodiments and modifications. As will become apparent to the person skilled in the art upon reading the foregoing description, all such further embodiments and modifications shall be covered by the present invention, as long as these do not depart from the general approach of the present invention and scope, as defined in the appended claims.

What is claimed is:

1. A supporting structure for concurrently supporting a plurality of containers having a predetermined length, the containers being used for the storage of substances for medical, pharmaceutical or cosmetic applications or contain such substances and each container having an upper end and a lower end, the supporting structure comprising a carrier having a plurality of supporting means and being configured to support and retain the containers on the carrier when in a first orientation and when in a second orientation opposite to the first orientation, wherein the supporting means comprises a protrusion that extends from a respective aperture of the carrier, wherein the protrusion is resilient and configured to pivot or flap away during insertion of the container into the aperture and supports the container in both the first orientation and the second orientation, wherein the supporting structure is formed in two parts comprising the carrier and a frame on which the carrier can be supported in a first carrier orientation or in a second carrier orientation opposite to the first carrier orientation, wherein when the containers are supported on the carrier in the first orientation and the carrier is supported on the frame in the first carrier orientation, the upper ends of the containers are arranged at a first distance to an upper rim of the frame, wherein when the containers are supported on the carrier in the second orientation and the carrier is supported on the frame in the second carrier orientation, the lower ends of the containers are arranged at a second distance to the upper rim of the frame, wherein the first distance is equal or substantially equal to the second distance, and wherein the upper ends and/or lower ends of the containers are accessible for a further processing of the containers, while they are supported on the carrier in the first orientation and in the second orientation.

2. The supporting structure according to claim 1, wherein the carrier comprises a plurality of apertures, wherein the supporting structure has a supporting means that is associated with the apertures, wherein the containers are supported by the supporting means on the carrier such
   that they extend through the apertures of the carrier,
   that the upper ends of the containers protrude beyond an upper rim of the carrier and/or
   that the lower ends of the containers protrude beyond a lower rim of the carrier.

3. The supporting structure according to claim 1, wherein in the first orientation and in the second orientation, the containers are supported on the carrier or physically and structurally retained in axial direction on the carrier.

4. The supporting structure according to claim 1, wherein the supporting structure has resilient supporting tongues that are provided-on the edge of the respective aperture and protrude from an upper surface of the carrier to support the respective container, and wherein
   the resilient supporting tongues are matched to the containers so that the containers are supported by the resilient supporting tongues with a radial clearance.

5. The supporting structure according to claim 4, wherein the resilient supporting tongues are biased towards a retaining position and are formed integral with the carrier.

6. The supporting structure according to claim 1, wherein the carrier has an underside with side walls or pins projecting from the underside of the carrier and substantially perpendicularly to prevent a contact of containers that are supported on the carrier directly adjacent to each other.

7. The supporting structure according to claim 6, wherein the side walls or pins are formed such that the containers are freely accessible from the underside of the carrier.

8. The supporting structure according to claim 6, wherein the side walls do not extend along the entire circumference of the containers, so that a portion of the containers supported on the carrier is accessible from the side of the carrier.

9. The supporting structure according to claim 1, wherein the carrier has an underside with side walls or pins projecting from the underside of the carrier, wherein the pins project essentially perpendicularly from the underside of the carrier to prevent a collision between containers supported on the carrier directly adjacent to each other, and wherein the supporting structure has supporting means that are configured such that the respective ends of the containers are supported on the supporting means.

10. The supporting structure according to claim 9, wherein the supporting means are formed as intersecting and interconnected supporting webs, wherein at least two supporting webs each span an aperture formed in the carrier.

11. The supporting structure according to claim 10, wherein in the region of a point of intersection of the intersecting supporting webs a recessed portion is formed to form a receptacle for a constricted neck portion of the container to be supported, for preventing a tilting of the containers supported on the carrier.

12. The supporting structure according to claim 11, wherein a difference between the distance to the upper rim of the frame used for supporting the carrier at which the upper ends of the containers are arranged in the first position and the distance to the upper rim of the frame used for supporting the carrier at which the lower ends of the containers are arranged in the second position corresponds to a length of constricted neck portions of the containers to be supported.

13. The supporting structure according to claim 1, further comprising members that cooperate with each other in a positive-fit manner disposed on the frame and on the carrier for defining a different height difference between the frame and the carrier in each of the first and second orientations.

14. A supporting structure for concurrently supporting a plurality of containers having a predetermined length, the containers being used for the storage of substances for medical, pharmaceutical or cosmetic applications or contain such substances and having upper ends and lower ends, the supporting structure comprising
   a trough-shaped carrier having a plurality of supporting means and being configured to support the containers on the trough-shaped carrier in a first orientation or in a second orientation opposite to the first orientation, wherein
   the supporting structure is formed in two parts comprising the trough-shaped carrier and a frame on which the trough-shaped carrier can be supported in a first carrier orientation or in a second carrier orientation opposite to the first carrier orientation,
   wherein when the containers are supported on the trough-shaped carrier in the first orientation or in the second orientation and the trough-shaped carrier is supported on the frame in the first carrier orientation, the upper ends of the containers are arranged at a first distance to the upper rim of the frame;
   wherein when the containers are supported on the trough-shaped carrier in the first orientation or in the second orientation and the trough-shaped carrier is supported on the frame in the second carrier orientation, the upper ends of the containers are arranged at a second distance to the upper rim of the frame;
   wherein the first distance is equal or substantially equal to the second distance,
   wherein the upper ends of the containers are accessible for a further processing of the containers, while the trough-shaped carrier is supported on the frame in the first carrier orientation and the containers are supported on the trough-shaped carrier in the first orientation or in the second orientation, or
   wherein the upper ends and/or lower ends of the containers are accessible for a further processing of the containers, while the trough-shaped carrier is supported on the frame in the second carrier orientation and the containers are supported on the trough-shaped carrier in the first orientation or in the second orientation.

15. The supporting structure according to claim 14, wherein the trough-shaped carrier comprises a plurality of apertures, wherein the supporting structure has support means that are associated with the apertures, wherein the containers are supported by the supporting means on the trough-shaped carrier such
   that they extend through the apertures of the trough-shaped carrier, and
   that the upper ends of the containers protrude beyond an upper rim of the trough-shaped carrier and/or
   that the lower ends of the containers protrude beyond a lower rim of the trough-shaped carrier.

16. The supporting structure according to claim 14, wherein in the first position and in second position the containers are supported on the trough-shaped carrier or retained in axial direction on the trough-shaped carrier.

17. The supporting structure according to claim 14, wherein the supporting structure has support means that are formed as resilient supporting tongues and are provided on the edge of a respective aperture and protrude from an upper surface of the trough-shaped carrier to support the respective container, and wherein the resilient supporting tongues are configured such that they are elastically pivoted away or flapped away during insertion of the containers into the apertures or receptacles, and the resilient supporting tongues are matched to the containers such that the containers are supported by the resilient supporting tongues with a radial clearance.

18. The supporting structure according to claim 17, wherein the resilient supporting tongues are biased towards a retaining position and are formed integral with the trough-shaped carrier.

19. The supporting structure according to claim 14, wherein the trough-shaped carrier has an underside with side walls or pins projecting from the underside of the trough-shaped carrier, and wherein the side walls or pins project from the underside of the trough-shaped carrier substantially perpendicularly to prevent a contact of containers that are supported on the trough-shaped carrier directly adjacent to each other.

20. The supporting structure according to claim 19, wherein the side walls or pins are formed such that the containers are freely accessible from the underside of the trough-shaped carrier.

21. The supporting structure according to claim 19, wherein the side walls do not extend along the entire circumference of the containers, so that a portion of the containers supported on the trough-shaped carrier is accessible from the side of the carrier.

22. The supporting structure according to claim 14, wherein the trough-shaped carrier has an underside with side walls or pins projecting from the underside of the trough-shaped carrier, wherein the pins project essentially perpendicularly from the underside of the trough-shaped carrier to prevent a collision between the containers supported on the trough-shaped carrier directly adjacent to each other, and wherein the supporting structure has support means that are configured such that the respective ends of the containers are supported on the supporting structure.

23. The supporting structure according to claim 22, wherein the supporting structure has supporting means that is formed as intersecting and interconnected supporting webs, and wherein at least two supporting webs each span an aperture formed in the trough-shaped carrier.

24. The supporting structure according to claim 23, wherein in a region of a point of intersection of the intersecting supporting webs, a recessed portion is formed to form a receptacle for a constricted neck portion of the container to be supported, for preventing a tilting of the container supported on the trough-shaped carrier.

25. The supporting structure according to claim 24, further comprising a difference between (a) the distance to the upper rim of the frame used for supporting the trough-shaped carrier at which the upper ends of the containers are arranged in the first carrier orientation and (b) the distance to the upper rim of the frame used for supporting the trough-shaped carrier at which the upper ends of the containers are arranged in the second carrier orientation corresponds to a length of the constricted neck portions of the containers to be supported.

26. The supporting structure according to claim 14, further comprising members that cooperate with each other in a positive-fit manner and are disposed on the frame and on the trough-shaped carrier for defining a different height difference between the frame and the trough-shaped carrier in the respective orientation.

* * * * *